US012773246B2

(12) United States Patent
Dayton et al.

(10) Patent No.: US 12,773,246 B2

(45) Date of Patent: Oct. 27, 2026

(54) BONE CUTTING GUIDE SYSTEMS AND METHODS

(71) Applicant: Treace Medical Concepts, Inc., Ponte Vedra, FL (US)

(72) Inventors: Paul Dayton, Ankeny, IA (US); Joe William Ferguson, Ponte Vedra Beach, FL (US); F. Barry Bays, Collierville, TN (US); John T. Treace, Ponte Vedra Beach, FL (US); W. Bret Smith, Lexington, SC (US)

(73) Assignee: Treace Medical Concepts, Inc., Ponte Vedra, FL (US)

( * ) Notice: Subject to any disclaimer, the term of this patent is extended or adjusted under 35 U.S.C. 154(b) by 0 days.

(21) Appl. No.: 18/642,470

(22) Filed: Apr. 22, 2024

(65) Prior Publication Data

US 2024/0268873 A1 Aug. 15, 2024

Related U.S. Application Data

(63) Continuation of application No. 17/106,306, filed on Nov. 30, 2020, now Pat. No. 11,963,703, which is a (Continued)

(51) Int. Cl.

| | |
|---|---|
| ***A61B 17/15*** | (2006.01) |
| ***A61B 17/56*** | (2006.01) |
| ***A61B 17/80*** | (2006.01) |

(52) U.S. Cl.

CPC .......... *A61B 17/8061* (2013.01); *A61B 17/15* (2013.01); *A61B 17/151* (2013.01); *A61B 2017/564* (2013.01)

(58) Field of Classification Search

CPC ................................................ A61B 2017/564

See application file for complete search history.

(56) References Cited

U.S. PATENT DOCUMENTS

| | | | |
|---|---|---|---|
| 3,664,022 | A | 5/1972 | Small |
| 4,069,824 | A | 1/1978 | Weinstock |

(Continued)

FOREIGN PATENT DOCUMENTS

| | | | |
|---|---|---|---|
| AU | 2009227957 B2 | 7/2014 | |
| CA | 2491824 A1 | 9/2005 | |

(Continued)

OTHER PUBLICATIONS

Dayton et al., "Dorsal Suspension Stitch: An Alternative Stabilization After Flexor Tenotomy for Flexible Hammer Digit Syndrome," The Journal of Foot and Ankle Surgery, vol. 48, No. 5, Sep./Oct. 2009, pp. 602-605.

(Continued)

*Primary Examiner* — David W Bates

(74) *Attorney, Agent, or Firm* — Fredrikson & Byron, P.A.

(57) ABSTRACT

A bone cutting guide may include a support that contains a shaft movable relative to the support. The shaft may carry a guide member having one or more cut guides through which a clinician inserts a cutting member to cut bone positioned under the guide cut guides. In operation, a clinician may fixate the support of the bone cutting guide to a bone and translate the guide member until the one or more cut guides are positioned at a desired cut location. The clinician may then perform a cut through the cut guide.

20 Claims, 13 Drawing Sheets

Related U.S. Application Data continuation of application No. 15/210,497, filed on Jul. 14, 2016, now Pat. No. 10,849,663.

(60) Provisional application No. 62/192,290, filed on Jul. 14, 2015.

(56) References Cited

U.S. PATENT DOCUMENTS

| | | | | |
|---|---|---|---|---|
| 4,159,716 | A | 7/1979 | Borchers | |
| 4,187,840 | A | 2/1980 | Watanabe | |
| 4,335,715 | A | 6/1982 | Kirkley | |
| 4,338,927 | A | 7/1982 | Volkov et al. | |
| 4,349,018 | A | 9/1982 | Chambers | |
| 4,364,381 | A | 12/1982 | Sher et al. | |
| 4,409,973 | A | 10/1983 | Neufeld | |
| 4,440,168 | A | 4/1984 | Warren | |
| 4,475,544 | A | 10/1984 | Reis | |
| 4,501,268 | A | 2/1985 | Comparetto | |
| 4,502,474 | A | 3/1985 | Comparetto | |
| 4,509,511 | A | 4/1985 | Neufeld | |
| 4,565,191 | A | 1/1986 | Slocum | |
| 4,570,624 | A | 2/1986 | Wu | |
| 4,627,425 | A | 12/1986 | Reese | |
| 4,628,919 | A | 12/1986 | Clyburn | |
| 4,632,102 | A | 12/1986 | Comparetto | |
| 4,664,102 | A | 5/1987 | Comparetto | |
| 4,708,133 | A | 11/1987 | Comparetto | |
| 4,736,737 | A | 4/1988 | Fargie et al. | |
| 4,750,481 | A | 6/1988 | Reese | |
| 4,754,746 | A | 7/1988 | Cox | |
| 4,757,810 | A | 7/1988 | Reese | |
| 4,895,141 | A | 1/1990 | Koeneman et al. | |
| 4,952,214 | A | 8/1990 | Comparetto | |
| 4,959,066 | A | 9/1990 | Dunn et al. | |
| 4,978,347 | A | 12/1990 | Ilizarov | |
| 4,988,349 | A | 1/1991 | Pennig | |
| 4,995,875 | A | 2/1991 | Coes | |
| 5,021,056 | A | 6/1991 | Hofmann et al. | |
| 5,035,698 | A | 7/1991 | Comparetto | |
| 5,042,983 | A | 8/1991 | Rayhack | |
| 5,049,149 | A | 9/1991 | Schmidt | |
| 5,053,039 | A | 10/1991 | Hofmann et al. | |
| 5,078,719 | A | 1/1992 | Schreiber | |
| 5,112,334 | A | 5/1992 | Alchermes et al. | |
| 5,122,140 | A | 6/1992 | Asche et al. | |
| 5,122,145 | A | 6/1992 | Fishbane | |
| 5,147,364 | A | 9/1992 | Comparetto | |
| 5,152,280 | A | 10/1992 | Danieli | |
| 5,176,685 | A | 1/1993 | Rayhack | |
| 5,207,676 | A | 5/1993 | Canadell et al. | |
| 5,246,444 | A | 9/1993 | Schreiber | |
| 5,254,119 | A | 10/1993 | Schreiber | |
| 5,304,177 | A | 4/1994 | Pennig | |
| 5,312,412 | A | 5/1994 | Whipple | |
| 5,350,382 | A | 9/1994 | Armstrong | |
| 5,358,504 | A | 10/1994 | Paley et al. | |
| 5,364,402 | A | 11/1994 | Mumme et al. | |
| 5,374,271 | A | 12/1994 | Hwang | |
| 5,413,579 | A | 5/1995 | Du Toit | |
| 5,417,694 | A | 5/1995 | Marik et al. | |
| 5,449,360 | A | 9/1995 | Schreiber | |
| 5,470,335 | A | 11/1995 | Du Toit | |
| 5,490,854 | A | 2/1996 | Fisher et al. | |
| 5,529,075 | A | 6/1996 | Clark | |
| 5,540,695 | A | 7/1996 | Levy | |
| 5,578,038 | A | 11/1996 | Slocum | |
| 5,586,564 | A | 12/1996 | Barrett et al. | |
| 5,601,565 | A | 2/1997 | Huebner | |
| 5,613,969 | A | 3/1997 | Jenkins, Jr. | |
| 5,620,442 | A | 4/1997 | Bailey et al. | |
| 5,620,448 | A | 4/1997 | Puddu | |
| 5,643,270 | A | 7/1997 | Combs | |
| 5,667,510 | A | 9/1997 | Combs | |
| 5,702,389 | A | 12/1997 | Taylor et al. | |
| H1706 | H | 1/1998 | Mason | |
| 5,722,978 | A | 3/1998 | Jenkins | |
| 5,749,875 | A | 5/1998 | Puddu | |
| 5,779,709 | A | 7/1998 | Harris et al. | |
| 5,788,695 | A | 8/1998 | Richardson | |
| 5,803,924 | A | 9/1998 | Oni et al. | |
| 5,810,822 | A | 9/1998 | Mortier | |
| 5,843,085 | A | 12/1998 | Graser | |
| 5,893,553 | A | 4/1999 | Pinkous | |
| 5,911,724 | A | 6/1999 | Wehrli | |
| 5,935,128 | A | 8/1999 | Carter et al. | |
| 5,941,877 | A | 8/1999 | Viegas et al. | |
| 5,947,973 | A | 9/1999 | Masini | |
| 5,951,556 | A | 9/1999 | Faccioli et al. | |
| 5,980,526 | A | 11/1999 | Johnson et al. | |
| 5,984,931 | A | 11/1999 | Greenfield | |
| 6,007,535 | A | 12/1999 | Rayhack et al. | |
| 6,027,504 | A | 2/2000 | McGuire | |
| 6,030,391 | A * | 2/2000 | Brainard | A61B 17/15 606/82 |
| 6,162,223 | A | 12/2000 | Orsak et al. | |
| 6,171,309 | B1 | 1/2001 | Huebner | |
| 6,203,545 | B1 | 3/2001 | Stoffella | |
| 6,248,109 | B1 | 6/2001 | Stoffella | |
| 6,391,031 | B1 | 5/2002 | Toomey | |
| 6,478,799 | B1 | 11/2002 | Williamson | |
| 6,511,481 | B2 | 1/2003 | von Hoffmann et al. | |
| 6,547,793 | B1 | 4/2003 | McGuire | |
| 6,676,662 | B1 | 1/2004 | Bagga et al. | |
| 6,719,773 | B1 | 4/2004 | Boucher et al. | |
| 6,743,233 | B1 | 6/2004 | Baldwin et al. | |
| 6,755,838 | B2 | 6/2004 | Trnka | |
| 6,796,986 | B2 | 9/2004 | Duffner | |
| 6,859,661 | B2 | 2/2005 | Tuke | |
| 7,018,383 | B2 | 3/2006 | McGuire | |
| 7,033,361 | B2 | 4/2006 | Collazo | |
| 7,097,647 | B2 | 8/2006 | Segler et al. | |
| 7,112,204 | B2 | 9/2006 | Justin et al. | |
| 7,153,310 | B2 | 12/2006 | Ralph et al. | |
| 7,182,766 | B1 | 2/2007 | Mogul | |
| 7,241,298 | B2 | 7/2007 | Nemec et al. | |
| 7,282,054 | B2 | 10/2007 | Steffensmeier et al. | |
| 7,377,924 | B2 | 5/2008 | Raistrick et al. | |
| 7,465,303 | B2 | 12/2008 | Riccione et al. | |
| 7,540,874 | B2 | 6/2009 | Trumble et al. | |
| 7,572,258 | B2 | 8/2009 | Stiernborg | |
| 7,635,365 | B2 | 12/2009 | Ellis et al. | |
| 7,641,660 | B2 | 1/2010 | Lakin et al. | |
| D610,257 | S | 2/2010 | Horton | |
| 7,686,811 | B2 | 3/2010 | Byrd et al. | |
| 7,691,108 | B2 | 4/2010 | Lavallee | |
| 7,763,026 | B2 | 7/2010 | Egger et al. | |
| D629,900 | S | 12/2010 | Fisher | |
| 7,967,823 | B2 | 6/2011 | Ammann et al. | |
| 7,972,338 | B2 | 7/2011 | O'Brien | |
| D646,389 | S | 10/2011 | Claypool et al. | |
| 8,057,478 | B2 | 11/2011 | Kuczynski et al. | |
| 8,062,301 | B2 | 11/2011 | Ammann et al. | |
| D651,315 | S | 12/2011 | Bertoni et al. | |
| D651,316 | S | 12/2011 | May et al. | |
| 8,080,010 | B2 | 12/2011 | Schulz et al. | |
| 8,080,045 | B2 | 12/2011 | Wotton, III | |
| 8,083,746 | B2 | 12/2011 | Novak | |
| 8,123,753 | B2 | 2/2012 | Poncet | |
| 8,137,406 | B2 | 3/2012 | Novak et al. | |
| 8,147,530 | B2 | 4/2012 | Strnad et al. | |
| 8,167,918 | B2 | 5/2012 | Strnad et al. | |
| 8,172,848 | B2 | 5/2012 | Tomko et al. | |
| 8,192,441 | B2 | 6/2012 | Collazo | |
| 8,197,487 | B2 | 6/2012 | Poncet et al. | |
| 8,231,623 | B1 | 7/2012 | Jordan | |
| 8,231,663 | B2 | 7/2012 | Kay et al. | |
| 8,236,000 | B2 | 8/2012 | Ammann et al. | |
| 8,246,561 | B1 | 8/2012 | Agee et al. | |
| D666,721 | S | 9/2012 | Wright et al. | |
| 8,262,664 | B2 | 9/2012 | Justin et al. | |
| 8,277,459 | B2 | 10/2012 | Sand et al. | |
| 8,282,644 | B2 | 10/2012 | Edwards | |
| 8,282,645 | B2 | 10/2012 | Lawrence et al. | |
| 8,292,966 | B2 | 10/2012 | Morton | |

(56) References Cited

U.S. PATENT DOCUMENTS 8,303,596 B2 11/2012 Plassky et al.
8,313,492 B2 11/2012 Wong et al.
8,323,289 B2 12/2012 Re
8,328,806 B2 12/2012 Tyber et al.
8,337,503 B2 12/2012 Lian
8,343,159 B2 1/2013 Bennett
8,377,105 B2 2/2013 Buescher
D679,395 S 4/2013 Wright et al.
8,409,209 B2 4/2013 Ammann et al.
8,435,246 B2 5/2013 Fisher et al.
8,475,462 B2 7/2013 Thomas et al.
8,496,662 B2 7/2013 Novak et al.
8,523,870 B2 9/2013 Green, II et al.
8,529,571 B2 9/2013 Horan et al.
8,540,777 B2 9/2013 Ammann et al.
8,545,508 B2 10/2013 Collazo
D694,884 S 12/2013 Mooradian et al.
D695,402 S 12/2013 Dacosta et al.
8,652,142 B2 2/2014 Geissler
8,657,820 B2 2/2014 Kubiak et al.
D701,303 S 3/2014 Cook
8,672,945 B2 3/2014 Lavallee et al.
8,696,716 B2 4/2014 Kartalian et al.
8,702,715 B2 4/2014 Ammann et al.
D705,929 S 5/2014 Frey
8,715,363 B2 5/2014 Ratron et al.
8,728,084 B2 5/2014 Berelsman et al.
8,758,354 B2 6/2014 Habegger et al.
8,764,760 B2 7/2014 Metzger et al.
8,764,763 B2 7/2014 Wong et al.
8,771,279 B2 7/2014 Philippon et al.
8,777,948 B2 7/2014 Bernsteiner
8,784,427 B2 7/2014 Fallin et al.
8,784,457 B2 7/2014 Graham
8,795,286 B2 8/2014 Sand et al.
8,801,727 B2 8/2014 Chan et al.
8,808,303 B2 8/2014 Stemniski et al.
8,828,012 B2 9/2014 May et al.
8,858,602 B2 10/2014 Weiner et al.
8,882,778 B2 11/2014 Ranft
8,882,816 B2 11/2014 Kartalian et al.
8,888,785 B2 11/2014 Ammann et al.
D720,456 S 12/2014 Dacosta et al.
8,900,247 B2 12/2014 Tseng et al.
8,906,026 B2 12/2014 Ammann et al.
8,945,132 B2 2/2015 Plassy et al.
8,979,926 B2 3/2015 Quinn et al.
8,998,903 B2 4/2015 Price et al.
8,998,904 B2 4/2015 Zeetser et al.
9,011,507 B2 4/2015 Schelling
9,023,052 B2 5/2015 Lietz et al.
9,044,250 B2 6/2015 Olsen et al.
9,060,822 B2 6/2015 Lewis et al.
9,089,376 B2 7/2015 Medoff et al.
9,101,421 B2 8/2015 Blacklidge
9,107,715 B2 8/2015 Blitz et al.
9,113,920 B2 8/2015 Ammann et al.
D740,424 S 10/2015 Dacosta et al.
9,220,518 B2 12/2015 Neal et al.
D765,844 S 9/2016 DaCosta
D766,434 S 9/2016 DaCosta
D766,437 S 9/2016 DaCosta
D766,438 S 9/2016 DaCosta
D766,439 S 9/2016 DaCosta
9,452,057 B2 9/2016 Dacosta et al.
9,522,023 B2 12/2016 Haddad et al.
9,750,538 B2 9/2017 Soffiatti et al.
9,785,747 B2 10/2017 Geebelen
9,980,760 B2 5/2018 Dacosta et al.
10,028,750 B2 7/2018 Rose
10,064,631 B2 9/2018 Dacosta et al.
10,159,499 B2 12/2018 Dacosta et al.
10,292,713 B2 5/2019 Fallin et al.
10,327,829 B2 6/2019 Dacosta et al.
10,376,268 B2 8/2019 Fallin et al.
10,470,779 B2 11/2019 Fallin et al.
10,779,867 B2 9/2020 Penzimer et al.
11,304,705 B2 4/2022 Fallin et al.
2001/0010818 A1* 8/2001 Engle .................... A61K 47/61 424/140.1
2002/0058944 A1 5/2002 Michelson
2002/0099381 A1 7/2002 Maroney
2002/0107519 A1 8/2002 Dixon et al.
2002/0165552 A1 11/2002 Duffner
2002/0198531 A1 12/2002 Millard et al.
2004/0010259 A1 1/2004 Keller et al.
2004/0039394 A1 2/2004 Conti et al.
2004/0097946 A1 5/2004 Dietzel et al.
2004/0138669 A1 7/2004 Horn
2005/0004676 A1 1/2005 Schon et al.
2005/0059978 A1 3/2005 Sherry et al.
2005/0070909 A1 3/2005 Egger et al.
2005/0075641 A1 4/2005 Singhatat et al.
2005/0101961 A1 5/2005 Huebner et al.
2005/0149042 A1 7/2005 Metzger
2005/0228389 A1 10/2005 Stiernborg
2005/0251147 A1 11/2005 Novak
2005/0267482 A1 12/2005 Hyde
2005/0273112 A1 12/2005 McNamara
2006/0036257 A1 2/2006 Steffensmeier
2006/0129163 A1 6/2006 McGuire
2006/0206044 A1 9/2006 Simon
2006/0217733 A1 9/2006 Plassky et al.
2006/0229621 A1 10/2006 Cadmus
2006/0241607 A1 10/2006 Myerson et al.
2006/0241608 A1 10/2006 Myerson et al.
2006/0247787 A1 11/2006 Rydell et al.
2006/0264961 A1 11/2006 Murray-Brown
2007/0010818 A1 1/2007 Stone et al.
2007/0123857 A1 5/2007 Deffenbaugh et al.
2007/0233138 A1 10/2007 Figueroa et al.
2007/0265634 A1 11/2007 Weinstein
2007/0276383 A1 11/2007 Rayhack
2008/0009863 A1 1/2008 Bond et al.
2008/0015603 A1 1/2008 Collazo
2008/0039850 A1 2/2008 Rowley et al.
2008/0091197 A1 4/2008 Coughlin
2008/0140081 A1 6/2008 Heavener et al.
2008/0147073 A1 6/2008 Ammann et al.
2008/0172054 A1 7/2008 Claypool et al.
2008/0195215 A1 8/2008 Morton
2008/0208252 A1 8/2008 Holmes
2008/0262500 A1 10/2008 Collazo
2008/0269908 A1 10/2008 Warburton
2008/0288004 A1 11/2008 Schendel
2009/0036893 A1 2/2009 Kartalian et al.
2009/0036931 A1 2/2009 Pech et al.
2009/0054899 A1 2/2009 Ammann et al.
2009/0093849 A1 4/2009 Grabowski
2009/0105767 A1 4/2009 Reiley
2009/0118733 A1 5/2009 Orsak et al.
2009/0198244 A1 8/2009 Leibel
2009/0198279 A1 8/2009 Zhang et al.
2009/0222047 A1 9/2009 Graham
2009/0254092 A1 10/2009 Albiol Llorach
2009/0254126 A1 10/2009 Orbay et al.
2009/0287309 A1 11/2009 Walch et al.
2010/0069910 A1 3/2010 Hasselman
2010/0121334 A1 5/2010 Couture et al.
2010/0130981 A1 5/2010 Richards
2010/0152782 A1 6/2010 Stone et al.
2010/0168799 A1 7/2010 Schumer
2010/0185245 A1 7/2010 Paul et al.
2010/0249779 A1 9/2010 Hotchkiss et al.
2010/0256687 A1 10/2010 Neufeld et al.
2010/0318088 A1 12/2010 Warne et al.
2010/0324556 A1 12/2010 Tyber et al.
2011/0009865 A1 1/2011 Orfaly
2011/0093084 A1 4/2011 Morton
2011/0118739 A1 5/2011 Tyber et al.
2011/0178524 A1 7/2011 Lawrence et al.
2011/0186456 A1 8/2011 Bertazzoni et al.
2011/0245835 A1 10/2011 Dodds et al.
2011/0264149 A1 10/2011 Pappalardo et al.

(56) References Cited

U.S. PATENT DOCUMENTS

2011/0288550 A1 11/2011 Orbay et al.
2011/0301648 A1 12/2011 Lofthouse et al.
2012/0016426 A1 1/2012 Robinson
2012/0029575 A1 2/2012 Orsak et al.
2012/0065689 A1 3/2012 Prasad et al.
2012/0078258 A1 3/2012 Lo et al.
2012/0123420 A1 5/2012 Honiball
2012/0123484 A1 5/2012 Lietz et al.
2012/0130376 A1 5/2012 Loring et al.
2012/0130382 A1 5/2012 Iannotti et al.
2012/0130383 A1 5/2012 Budoff
2012/0184961 A1 7/2012 Johannaber
2012/0185056 A1 7/2012 Warburton
2012/0191199 A1 7/2012 Raemisch
2012/0239045 A1 9/2012 Li
2012/0253350 A1 10/2012 Anthony et al.
2012/0265301 A1 10/2012 Demers et al.
2012/0277745 A1 11/2012 Lizee
2012/0303033 A1* 11/2012 Weiner ............... A61B 17/1775 606/87
2012/0330135 A1 12/2012 Millahn et al.
2013/0012949 A1* 1/2013 Fallin ................... A61B 17/151 606/87
2013/0030438 A1 1/2013 Fox
2013/0035694 A1 2/2013 Grimm et al.
2013/0085499 A1 4/2013 Lian
2013/0085502 A1 4/2013 Harrold
2013/0096563 A1 4/2013 Meade et al.
2013/0131821 A1 5/2013 Cachia
2013/0150900 A1 6/2013 Haddad et al.
2013/0150903 A1 6/2013 Vincent
2013/0158556 A1 6/2013 Jones et al.
2013/0165936 A1 6/2013 Myers
2013/0165938 A1 6/2013 Chow et al.
2013/0172942 A1 7/2013 Lewis et al.
2013/0184714 A1 7/2013 Kaneyama et al.
2013/0190765 A1 7/2013 Harris et al.
2013/0190766 A1 7/2013 Harris et al.
2013/0204259 A1 8/2013 Zajac
2013/0226248 A1 8/2013 Hatch et al.
2013/0226252 A1 8/2013 Mayer
2013/0231668 A1 9/2013 Olsen et al.
2013/0237987 A1 9/2013 Graham
2013/0237989 A1 9/2013 Bonutti
2013/0267956 A1 10/2013 Terrill et al.
2013/0310836 A1 11/2013 Raub et al.
2013/0325019 A1 12/2013 Thomas et al.
2013/0325076 A1 12/2013 Palmer et al.
2013/0331845 A1 12/2013 Horan et al.
2013/0338785 A1 12/2013 Wong
2014/0005672 A1 1/2014 Edwards et al.
2014/0025127 A1 1/2014 Richter
2014/0031882 A1 1/2014 Schmuck et al.
2014/0039501 A1 2/2014 Schickendantz et al.
2014/0039561 A1 2/2014 Weiner et al.
2014/0046387 A1 2/2014 Waizenegger
2014/0074099 A1 3/2014 Vigneron et al.
2014/0074101 A1 3/2014 Collazo
2014/0094861 A1 4/2014 Fallin
2014/0094924 A1 4/2014 Hacking et al.
2014/0135775 A1 5/2014 Maxson et al.
2014/0163563 A1 6/2014 Reynolds et al.
2014/0171953 A1 6/2014 Gonzalvez et al.
2014/0180342 A1 6/2014 Lowery et al.
2014/0188139 A1 7/2014 Fallin et al.
2014/0194884 A1 7/2014 Martin et al.
2014/0194999 A1* 7/2014 Orbay ................ A61B 17/8095 606/85
2014/0207144 A1 7/2014 Lee et al.
2014/0249537 A1 9/2014 Wong et al.
2014/0257308 A1 9/2014 Johannaber
2014/0257509 A1 9/2014 Dacosta et al.
2014/0276815 A1 9/2014 Riccione
2014/0276853 A1 9/2014 Long et al.
2014/0277176 A1 9/2014 Buchanan et al.
2014/0277214 A1 9/2014 Helenbolt et al.
2014/0288562 A1 9/2014 Von Zabern et al.
2014/0296995 A1 10/2014 Reiley et al.
2014/0303621 A1 10/2014 Gerold et al.
2014/0336658 A1 11/2014 Luna et al.
2014/0343555 A1 11/2014 Russi et al.
2014/0350561 A1 11/2014 Dacosta et al.
2015/0032168 A1 1/2015 Orsak et al.
2015/0045801 A1 2/2015 Axelson, Jr. et al.
2015/0045839 A1 2/2015 Dacosta et al.
2015/0051650 A1 2/2015 Verstreken et al.
2015/0057667 A1 2/2015 Ammann et al.
2015/0066094 A1 3/2015 Prandi et al.
2015/0112446 A1 4/2015 Melamed et al.
2015/0119944 A1 4/2015 Geldwert
2015/0142064 A1 5/2015 Perez et al.
2015/0150608 A1 6/2015 Sammarco
2015/0182273 A1 7/2015 Stemniski et al.
2015/0223851 A1 8/2015 Hill et al.
2015/0245858 A1* 9/2015 Weiner ............... A61B 17/8061 606/280
2016/0015426 A1 1/2016 Dayton
2016/0022315 A1 1/2016 Soffiatti et al.
2016/0135858 A1 5/2016 Dacosta et al.
2016/0151165 A1 6/2016 Fallin et al.
2016/0175089 A1 6/2016 Fallin et al.
2016/0192950 A1 7/2016 Dayton et al.
2016/0199076 A1 7/2016 Fallin et al.
2016/0213384 A1 7/2016 Fallin et al.
2016/0235414 A1* 8/2016 Hatch ................ A61B 17/1739
2016/0242791 A1 8/2016 Fallin et al.
2016/0256204 A1 9/2016 Patel et al.
2016/0324532 A1 11/2016 Montoya et al.
2016/0354127 A1 12/2016 Lundquist et al.
2017/0042598 A1* 2/2017 Santrock ............ A61B 17/1775
2017/0042599 A1* 2/2017 Bays .................. A61B 17/8061
2017/0056031 A1 3/2017 Awtrey et al.
2017/0079669 A1 3/2017 Bays et al.
2017/0143511 A1 5/2017 Cachia
2017/0164989 A1 6/2017 Weiner et al.
2017/0172638 A1* 6/2017 Santrock ............ A61B 17/1728
2018/0132868 A1 5/2018 Dacosta et al.
2018/0344334 A1 12/2018 Kim et al.
2020/0029977 A1* 1/2020 Dayton ................ A61B 17/151
2021/0077120 A1* 3/2021 Hatch ................ A61B 17/1739
2021/0093328 A1* 4/2021 Dayton .................. A61B 17/15
2021/0196324 A1* 7/2021 Dayton .............. A61B 17/6416
2022/0079645 A1* 3/2022 Smith ................ A61B 17/1682
2024/0268836 A1* 8/2024 Dayton .................. A61B 17/15

FOREIGN PATENT DOCUMENTS

CA 2854997 A1 5/2013
CH 695846 A5 9/2006
CN 2930668 Y 8/2007
CN 201558162 U 8/2010
CN 201572172 U 9/2010
CN 201586060 U 9/2010
CN 201912210 U 8/2011
CN 101237835 B 11/2012
CN 202801773 U 3/2013
CN 103462675 A 12/2013
CN 103505276 A 1/2014
CN 203458450 U 3/2014
CN 103735306 A 4/2014
CN 102860860 B 5/2014
CN 203576647 U 5/2014
CN 104490460 A 4/2015
CN 104510523 A 4/2015
CN 104523327 A 4/2015
CN 104546102 A 4/2015
CN 204379413 U 6/2015
CN 204410951 U 6/2015
CN 204428143 U 7/2015
CN 204428144 U 7/2015
CN 204428145 U 7/2015
CN 204446081 U 7/2015
DE 202006010241 U1 3/2007
DE 102007053058 B3 4/2009

(56) References Cited

FOREIGN PATENT DOCUMENTS

| | | | |
|---|---|---|---|
| EP | 685206 | B1 | 9/2000 |
| EP | 1508316 | B1 | 5/2007 |
| EP | 1897509 | B1 | 7/2009 |
| EP | 2124772 | A1 | 12/2009 |
| EP | 2124832 | B1 | 8/2012 |
| EP | 2632349 | A1 | 9/2013 |
| EP | 2665428 | A1 | 11/2013 |
| EP | 2742878 | A1 | 6/2014 |
| EP | 2750617 | A1 | 7/2014 |
| EP | 2849684 | A1 | 3/2015 |
| EP | 2624764 | B1 | 12/2015 |
| EP | 3023068 | A2 | 5/2016 |
| FR | 2362616 | A1 | 3/1978 |
| FR | 2764183 | B1 | 11/1999 |
| FR | 2953120 | B1 | 1/2012 |
| FR | 3030221 | A1 | 6/2016 |
| GB | 2154143 | A | 9/1985 |
| GB | 2154144 | A | 9/1985 |
| GB | 2334214 | B | 1/2003 |
| IN | 200903719 | P1 | 6/2009 |
| IN | 200904479 | P2 | 5/2010 |
| IN | 140/DELNP/2012 | P1 | 2/2013 |
| IN | 2004/KOLNP/2013 | P2 | 11/2013 |
| JP | S635739 | A | 1/1988 |
| JP | H0531116 | A | 2/1993 |
| JP | 2004174265 | A | 6/2004 |
| JP | 2006158972 | A | 6/2006 |
| JP | 4134243 | B2 | 8/2008 |
| JP | 2008537498 | A | 9/2008 |
| JP | 4162380 | B2 | 10/2008 |
| JP | 2011092405 | A | 5/2011 |
| JP | 2011523889 | A | 8/2011 |
| JP | 4796943 | B2 | 10/2011 |
| JP | 5466647 | B2 | 4/2014 |
| JP | 2014511207 | A | 5/2014 |
| JP | 2014521384 | A | 8/2014 |
| JP | 5628875 | B2 | 11/2014 |
| KR | 100904142 | B1 | 6/2009 |
| MD | 756 | Z | 11/2014 |
| RU | 2098036 | C1 | 12/1997 |
| RU | 2195892 | C2 | 1/2003 |
| RU | 2320287 | C1 | 3/2008 |
| RU | 2321366 | C2 | 4/2008 |
| RU | 2321369 | C1 | 4/2008 |
| RU | 2346663 | C2 | 2/2009 |
| RU | 2412662 | C1 | 2/2011 |
| SU | 1333328 | A2 | 8/1987 |
| WO | 0166022 | A1 | 9/2001 |
| WO | 03075775 | A1 | 9/2003 |
| WO | 2004089227 | A2 | 10/2004 |
| WO | 2008051064 | A1 | 5/2008 |
| WO | 2009029798 | A1 | 3/2009 |
| WO | 2009032101 | A2 | 3/2009 |
| WO | 2011037885 | A1 | 3/2011 |
| WO | 2012004798 | A1 | 1/2012 |
| WO | 2012029008 | A1 | 3/2012 |
| WO | 2012103335 | A1 | 8/2012 |
| WO | 2013090392 | A1 | 6/2013 |
| WO | 2013134387 | A1 | 9/2013 |
| WO | 2013169475 | A1 | 11/2013 |
| WO | 2014020561 | A1 | 2/2014 |
| WO | 2014022055 | A1 | 2/2014 |
| WO | 2014035991 | A1 | 3/2014 |
| WO | 2014085882 | A1 | 6/2014 |
| WO | 2014147099 | A1 | 9/2014 |
| WO | 2014152219 | A2 | 9/2014 |
| WO | 2014152535 | A1 | 9/2014 |
| WO | 2014177783 | A1 | 11/2014 |
| WO | 2014200017 | A1 | 12/2014 |
| WO | 2015094409 | A1 | 6/2015 |
| WO | 2015105880 | A1 | 7/2015 |
| WO | 2015123270 | A1 | 8/2015 |
| WO | 2015127515 | A2 | 9/2015 |
| WO | 2016134160 | A1 | 8/2016 |

OTHER PUBLICATIONS

Dayton et al., "The Extended Knee Hemilithotomy Position for Gastrocnemius Recession," The Journal of Foot and Ankle Surgery, vol. 49, 2010, pp. 214-216.

Wienke et al., "Bone Stimulation For Nonunions: What the Evidence Reveals," Podiatry Today, vol. 24, No. 9, Sep. 2011, pp. 52-57.

Dayton et al., "Hallux Varus as Complication of Foot Compartment Syndrome," The Journal of Foot and Ankle Surgery, vol. 50, 2011, pp. 504-506.

Dayton et al., "Measurement of Mid-Calcaneal Length on Plain Radiographs: Reliability of a New Method," Foot and Ankle Specialist, vol. 4, No. 5, Oct. 2011, pp. 280-283.

Dayton et al., "A User-Friendly Method of Pin Site Management for External Fixators," Foot and Ankle Specialist, Sep. 16, 2011, 4 pages.

Dayton et al., "Effectiveness of a Locking Plate in Preserving Midcalcaneal Length and Positional Outcome after Evans Calcaneal Osteotomy: A Retrospective Pilot Study," The Journal of Foot and Ankle Surgery, vol. 52, 2013, pp. 710-713.

Dayton et al., "Does Postoperative Showering or Bathing of a Surgical Site Increase the Incidence of Infection? A Systematic Review of the Literature," The Journal of Foot and Ankle Surgery, vol. 52, 2013, pp. 612-614.

Dayton et al., "Technique for Minimally Invasive Reduction of Calcaneal Fractures Using Small Bilateral External Fixation," The Journal of Foot and Ankle Surgery, Article in Press, 2014, 7 pages.

Dayton et al., "Clarification of the Anatomic Definition of the Bunion Deformity," The Journal of Foot and Ankle Surgery, vol. 53, 2014, pp. 160-163.

Dayton et al., "Observed Changes in Radiographic Measurements of the First Ray after Frontal Plane Rotation of the First Metatarsal in a Cadaveric Foot Model," The Journal of Foot and Ankle Surgery, Article in Press, 2014, 5 pages.

Dayton et al., "Observed Changes in First Metatarsal and Medial Cuneiform Positions after First Metatarsophalangeal Joint Arthrodesis," The Journal of Foot and Ankle Surgery, vol. 53, 2014, pp. 32-35.

Dayton et al., "Reduction of the Intermetatarsal Angle after First Metatarsal Phalangeal Joint Arthrodesis: A Systematic Review," The Journal of Foot and Ankle Surgery, Article in Press, 2014, 4 pages.

Feilmeier et al., "Reduction of Intermetatarsal Angle after First Metatarsophalangeal Joint Arthrodesis in Patients with Hallux Valgus," The Journal of Foot and Ankle Surgery, vol. 53, 2014, pp. 29-31.

Dayton et al., "Principles of Management of Growth Plate Fractures in the Foot and Ankle," Clinics in Podiatric Medicine and Surgery, Pediatric Foot Deformities, Oct. 2013, 17 pages.

Dayton et al., "Observed Changes in Radiographic Measurements of the First Ray after Frontal and Transverse Plane Rotation of the Hallux: Does the Hallux Drive the Metatarsal in a Bunion Deformity?," The Journal of Foot and Ankle Surgery, Article in Press, 2014, 4 pages.

Rodriguez et al., "Ilizarov method of fixation for the management of pilon and distal tibial fractures in the compromised diabetic patient: A technique guide," The Foot and Ankle Journal Online, vol. 7, No. 2, 2014, 9 pages.

Feilmeier et al., "Incidence of Surgical Site Infection in the Foot and Ankle with Early Exposure and Showering of Surgical Sites: A Prospective Observation," The Journal of Foot and Ankle Surgery, vol. 53, 2014, pp. 173-175.

Catanese et al., "Measuring Sesamoid Position in Hallux Valgus: When Is the Sesamoid Axial View Necessary," Foot and Ankle Specialist, 2014, 3 pages.

Dayton et al., "Comparison of Complications for Internal and External Fixation for Charcot Reconstruction: A Systematic Review," The Journal of Foot and Ankle Surgery, Article in Press, 2015, 4 pages.

Dayton et al., "A new triplanar paradigm for bunion management," Lower Extremity Review, Apr. 2015, 9 pages.

Dayton et al., "American College of Foot and Ankle Surgeons' Clinical Consensus Statement: Perioperative Prophylactic Antibi-

(56) References Cited

OTHER PUBLICATIONS otic Use in Clean Elective Foot Surgery," The Journal of Foot and Ankle Surgery, Article in Press, 2015, 7 pages.
Dayton et al., "Complications of Metatarsal Suture Techniques for Bunion Correction: A Systematic Review of the Literature," The Journal of Foot and Ankle Surgery, Article in Press, 2015, 3 pages.
DeCarbo et al., "The Weil Osteotomy: A Refresher," Techniques in Foot and Ankle Surgery, vol. 13, No. 4, Dec. 2014, pp. 191-198.
DeCarbo et al., "Resurfacing Interpositional Arthroplasty for Degenerative Joint Diseas of the First Metatarsalphalangeal Joint," Podiatry Management, Jan. 2013, pp. 137-142.
DeCarbo et al., "Locking Plates: Do They Prevent Complications?," Podiatry Today, Apr. 2014, 7 pages.
Easley et al., "Current Concepts Review: Hallux Valgus Part II: Operative Treatment," Foot and Ankle International, vol. 28, No. 6, Jun. 2007, pp. 748-758.
KIM et lal., "A Multicenter Retrospective Review of Outcomes for Arthrodesis, Hemi-Metallic Joint Implant, and Resectional Arthroplasty in the Surgical Treatment of End-Stage Hallux Rigidus," The Journal of Foot and Ankle Surgery, vol. 51, 2012, pp. 50-56.
Easley et al., "Current Concepts Review: Hallux Valgus Part I: Pathomechanics, Clinical Assessment, and Nonoperative Management," Foot and Ankle International, vol. 28, No. 5, May 2007, pp. 654-659.
Sandhu et al., "Digital Arthrodesis With a One-Piece Memory Nitinol Intramedullary Fixation Device: A Retrospective Review," Foot and Ankle Specialist, vol. 6, No. 5, Oct. 2013, pp. 364-366.
Weber et al., "Use of the First Ray Splay Test to Assess Transverse Plane Instability Before First Metatarsocuneiform Fusion," The Journal of Foot and Ankle Surgery, vol. 45, No. 4, Jul./Aug. 2006, pp. 278-282.
Smith et al., "Opening Wedge Osteotomies for Correction of Hallux Valgus: A Review of Wedge Plate Fixation," Foot and Ankle Specialist, vol. 2, No. 6, Dec. 2009, pp. 277-282.
Easley et al., "What is the Best Treatment for Hallux Valgus?," Evidence-Based Orthopaedics—The Best Answers to Clinical Questions, Chapter 73, 2009, pp. 479-491.
Shurnas et al., "Proximal Metatarsal Opening Wedge Osteotomy," Operative Techniques in Foot and Ankle Surgery, Section I, Chapter 13, 2011, pp. 73-78.
Coetzee et al., "Revision Hallux Valgus Correction," Operative Techniques in Foot and Ankle Surgery, Section I, Chapter 15, 2011, pp. 84-96.
Le et al., "Tarsometatarsal Arthrodesis," Operative Techniques in Foot and Ankle Surgery, Section II, Chapter 40, 2011, pp. 281-285.
Collan et al., "The biomechanics of the first metatarsal bone in hallux valgus: A preliminary study utilizing a weight bearing extremity CT," Foot and Ankle Surgery, vol. 19, 2013, pp. 155-161.
Eustace et al., "Hallux valgus, first metatarsal pronation and collapse of the medial longitudinal arch—a radiological correlation," Skeletal Radiology, vol. 23, 1994, pp. 191-194.
Mizuno et al., "Detorsion Osteotomy of the First Metatarsal Bone in Hallux Valgus," Japanese Orthopaedic Association, Tokyo, 1956; 30:813-819.
Okuda et al., "The Shape of the Lateral Edge of the First Metatarsal Head as a Risk Factor for Recurrence of Hallux Valgus," The Journal of Bone and Joint Surgery, vol. 89, 2007, pp. 2163-2172.
Okuda et al., "Proximal Metatarsal Osteotomy for Hallux Valgus: Comparison of Outcome for Moderate and Severe Deformities," Foot and Ankle International, vol. 29, No. 7, Jul. 2008, pp. 664-670.
D'Amico et al., "Motion of the First Ray: Clarification Through Investigation," Journal of the American Podiatry Association, vol. 69, No. 1, Jan. 1979, pp. 17-23.
Groves, "Operative Report," St. Tammany Parish Hospital, Date of Procedure, Mar. 26, 2014, 2 pages.
Claim Chart for Groves Public Use (Mar. 26, 2014), Exhibit B4 of Defendant Fusion Orthopedics LLC's Invalidity Contentions, No. CV-22-00490-PHX-SRB, US District Court for the District of Arizona, Aug. 27, 2022, 161 pages.
Defendant Fusion Orthopedics LLC's Invalidity Contentions, No. CV-22-00490-PHX-SRB, US District Court for the District of Arizona, Aug. 27, 2022, 41 pages.
Prior Art Publications, Exhibit A of Defendant Fusion Orthopedics LLC's Invalidity Contentions, No. CV-22-00490-PHX-SRB, US District Court for the District of Arizona, Aug. 27, 2022, 3 pages.
Claim Chart for Fishco, "Making the Lapidus Easy," The Podiatry Institute (Apr. 2014), Exhibit B1 of Defendant Fusion Orthopedics LLC's Invalidity Contentions, No. CV-22-00490-PHX-SRB, US District Court for the District of Arizona, Aug. 27, 2022, 97 pages.
Claim Chart for Fishco, "A Straightforward Guide to the Lapidus Bunionectomy," HMP Global (Sep. 6, 2013), Exhibit B2 of Defendant Fusion Orthopedics LLC's Invalidity Contentions, No. CV-22-00490-PHX-SRB, US District Court for the District of Arizona, Aug. 27, 2022, 67 pages.
Claim Chart for Groves, "Functional Position Joint Sectioning: Pre-Load Method for Lapidus Arthrodesis," Update 2015: Proceedings of the Annual Meeting of the Podiatry Institute, Chpt. 6, pp. 23-29 (Apr. 2015), Exhibit B3 of Defendant Fusion Orthopedics LLC's Invalidity Contentions, No. CV-22-00490-PHX-SRB, US District Court for the District of Arizona, Aug. 27, 2022, 151 pages.
Claim Chart for Mote, "First Metatarsal-Cuneiform Arthrodesis for the Treatment of First Ray Pathology: A Technical Guide," The Journal Foot & Ankle Surgery (Sep. 1, 2009), Exhibit B5 of Defendant Fusion Orthopedics LLC's Invalidity Contentions, No. CV-22-00490-PHX-SRB, US District Court for the District of Arizona, Aug. 27, 2022, 21 pages.
Claim Chart for U.S. Pat. No. 10,376,268 to Fallin et al., entitled "Indexed Tri-Planar Osteotomy Guide and Method," issued Aug. 13, 2019, Exhibit B6 of Defendant Fusion Orthopedics LLC's Invalidity Contentions, No. CV-22-00490-PHX-SRB, US District Court for the District of Arizona, Aug. 27, 2022, 155 pages.
Claim Chart for U.S. Pat. No. 8,282,645 to Lawrence et al., entitled "Metatarsal Bone Implant Cutting Guide," issued Jan. 18, 2010, Exhibit B7 of Defendant Fusion Orthopedics LLC's Invalidity Contentions, No. CV-22-00490-PHX-SRB, US District Court for the District of Arizona, Aug. 27, 2022, 76 pages.
Claim Chart for U.S. Pat. No. 9,452,057 to Dacosta et al., entitled "Bone Implants and Cutting Apparatuses and Methods," issued Apr. 8, 2011, Exhibit B8 of Defendant Fusion Orthopedics LLC's Invalidity Contentions, No. CV-22-00490-PHX-SRB, US District Court for the District of Arizona, Aug. 27, 2022, 110 pages.
Obviousness Chart, Exhibit C of Defendant Fusion Orthopedics LLC's Invalidity Contentions, No. CV-22-00490-PHX-SRB, US District Court for the District of Arizona, Aug. 27, 2022, 153 pages.
"Foot and Ankle Instrument Set," Smith & Nephew, 2013, 2 pages.
"Lapidus Pearls: Gaining Joint Exposure to Decrease Non-Union," Youtube, Retrieved online from <https://www.youtube.com/watch?v=-jqJyE7pj-Y>, dated Nov. 2, 2009, 3 pages.
"Reconstructive Surgery of the Foot & Ankle," The Podiatry Institute, Update 2015, Conference Program, May 2015, 28 pages.
"Speed Continuous Active Compression Implant," BioMedical Enterprises, Inc., A120-029 Rev. 3, 2013, 4 pages.
"Visionaire: Patient Matched Cutting Blocks Surgical Procedure," Smith & Nephew, Inc., 2009, 2 pages.
Arthrex, "Comprehensive Foot System," Retrieved online from <https://www.arthrex.com/resources/animation/8U3iaPvY6kO8bwFAwZF50Q/comprehensive-foot-system?referringTeam=foot_and_ankle>, dated Aug. 27, 2013, 3 pages.
Baravarian, "Why the Lapidus Procedure is Ideal for Bunions," Podiatry Today, Retrieved online from <https://www.hmpglobal-learhmpgloballe.com/site/podipodi/article/5542>, dated May 2006, 8 pages.
Bauer et al., "Offset-V Osteotomy of the First Metatarsal Shaft in Hallux Abducto Valgus," McGlamry's Comprehensive Textbook of Foot and Ankle Surgery, Fourth Edition, vol. 1, Chapter 29, 2013, 26 pages.
Cottom, "Fixation of the Lapidus Arthrodesis with a Plantar Interfragmentary Screw and Medial Low Profile Locking Plate," The Journal of Foot & Ankle Surgery, vol. 51, 2012, pp. 517-522.
Coughlin, "Fixation of the Lapidus Arthrodesis with a Plantar Interfragmentary Screw and Medial Low Profile Locking Plate, "Orthopaedics and Traumatology, vol. 7, 1999, pp. 133-143.

(56) References Cited

OTHER PUBLICATIONS

Dayton et al., "Observed Changes in Radiographic Measurements of the First Ray after Frontal Plane Rotation of the First Metatarsal in a Cadaveric Foot Model," The Journal of Foot & Ankle Surgery, vol. 53, 2014, pp. 274-278.
Dayton et al., "Relationship of Frontal Plane Rotation of First Metatarsal to Proximal Articular Set Angle and Hallux Alignment in Patients Undergoing Tarsometatarsal Arthrodesis for Hallux Abducto Valgus: A Case Series and Critical Review of the Literature," The Journal of Foot & Ankle Surgery, 2013, Article in Press, Mar. 1, 2013, 7 pages.
DiDomenico et al., "Lapidus Bunionectomy: First Metatarsal-Cuneiform Arthrodesis," McGlamry's Comprehensive Textbook of Foot and Ankle Surgery, Fourth Edition, vol. 1, Chapter 31, 2013, 24 pages.
Fallin et al., US Provisional Application Entitled Indexed Tri-Planar Osteotomy Guide and Method, U.S. Appl. No. 62/118,378, filed Feb. 19, 2015, 62 pages.
Fishco, "A Straightforward Guide To The Lapidus Bunionectomy, "Podiatry Today, Retrieved online from <https:// www.hmpgloballearningnetwork.com/site/podiatry/blogged/straightforward-guide-lapidus-bunionectomy>, dated Sep. 6, 2013, 5 pages.
Fishco, "Making the Lapidus Easy," The Podiatry Institute, Update 2014, Chapter 14, 2014, pp. 91-93.
Fleming et al., "Results of Modified Lapidus Arthrodesis Procedure Using Medial Eminence as an Interpositional Autograft," The Journal of Foot & Ankle Surgery, vol. 50, 2011, pp. 272-275.
Fuhrmann, "Arthrodesis of the First Tarsometatarsal Joint for Correction of the Advanced Splayfoot Accompanied by a Hallux Valgus," Operative Orthopadie und Traumatologie, No. 2, 2005, pp. 195-210.
Gerard et al., "The Modified Lapidus Procedure," Orthopedics, vol. 31, No. 3, Mar. 2008, 7 pages.
Giannoudis et al., "Hallux Valgus Correction," Practical Procedures in Elective Orthopaedic Surgery, Pelvis and Lower Extremity, Chapter 38, 2012, 22 pages.
Greiner, "The Jargon of Pedal Movements," Foot & Ankle International, vol. 28, No. 1, Jan. 2007, pp. 109-125.
Groves, "Functional Position Joint Sectioning: Pre-Load Method for Lapidus Arthrodesis," The Podiatry Institute, Update 2015, Chapter 6, 2015, pp. 23-29.
Hardy et al., "Observations on Hallux Valgus," The Journal of Bone and Joint Surgery, vol. 33B, No. 3, Aug. 1951, pp. 376-391.
Holmes, Jr., "Correction of the Intermetatarsal Angle Component of Hallux Valgus Using Fiberwire-Attached Endo-buttons," Revista Internacional de Ciencias Podologicas, vol. 6, No. 2, 2012, pp. 73-79.
Integra, "Integra Large Qwix Positioning and Fixation Screw, Surgical Technique," 2012, 16 pages.
Kilmartin et al., "Combined rotation scarf and Akin osteotomies for hallux valgus: a patient focused 9 year follow up of 50 patients," Journal of Foot and Ankle Research, vol. 3, No. 2, 2010, 12 pages.
Lee et al., "Technique Tip: Lateral Soft-Tissue Release for Correction of Hallux Valgus Through a Medial Incision Using A Dorsal Flap Over the First Metatarsal," Foot & Ankle International, vol. 28, No. 8, Aug. 2007, pp. 949-951.
Mote et al., "First Metatarsal-Cuneiform Arthrodesis for the Treatment of First Ray Pathology: A Technical Guide," JFAS Techniques Guide, vol. 48, No. 5, Sep./Oct. 2009, pp. 593-601.
Myerson, "Cuneiform-Metatarsal Arthrodesis," The Foot and Ankle, Chapter 9, 1997, pp. 107-117.
Sammarco, "Surgical Strategies: Mau Osteotomy for Correction of Moderate and Severe Hallux Valgus Deformity," Foot & Ankle International, vol. 28, No. 7, Jul. 2007, pp. 857-864.
Schon et al., "Cuneiform-Metatarsal Arthrodesis for Hallux Valgus, "The Foot and Ankle, Second Edition, Chapter 8, 2002, pp. 99-117.
Sokoloff, "Lapidus Procedure," Textbook of Bunion Surgery, Chapter 15, 1981, pp. 277-287.
Stamatis et al., "Mini Locking Plate as "Medial Buttress" for Oblique Osteotomy for Hallux Valgus," Foot & Ankle International, vol. 31, No. 10, Oct. 2010, pp. 920-922.
Stewart, "Use for BME Speed Nitinol Staple Fixation for the Lapidus Procedure," date unknown, 1 page.
Wukich et al., "Hypermobility of the First Tarsometatarsal Joint," Foot and Ankle Clinics, vol. 10, No. 1, Mar. 2005, pp. 157-166.
Dayton et al., "Biwinged Excision for Round Pedal Lesions," The Journal of Foot and Ankle Surgery, vol. 35, No. 3, 1996, pp. 244-249.
Dayton et al., "Medial Incision Approach to the First Metatarsophalangeal Joint," The Journal of Foot and Ankle Surgery, vol. 40, No. 6, Nov./Dec. 2001, pp. 414-417.
Dayton et al., "Reduction of the Intermetatarsal Angle after First Metatarsophalangeal Joint Arthrodesis in Patients with Moderate and Severe Metatarsus Primus Adductus," The Journal of Foot and Ankle Surgery, vol. 41, No. 5, Sep./Oct. 2002, pp. 316-319.
Dayton et al., "Use of the Z Osteotomy for Tailor Bunionectomy," The Journal of Foot and Ankle Surgery, vol. 42, No. 3, May/Jun. 2003, pp. 167-169.
Dayton et al., "Early Weightbearing After First Metatarsophalangeal Joint Arthrodesis: A Retrospective Observational Case Analysis," The Journal of Foot and Ankle Surgery, vol. 43, No. 3, May/Jun. 2004, pp. 156-159.
Nagy et al., "The AO Ulnar Shortening Osteotomy System Indications and Surgical Technique," Journal of Wrist Surgery, vol. 3, No. 2, 2014, pp. 91-97.
NexFix from Nexa Orthopedics, MetaFix I from Merete Medical, Inc. and The BioPro Lower Extremities from BioPro, found in Foot & Ankle International Journal, vol. 28, No. 1, Jan. 2007, 4 pages.
Odenbring et al., "A guide instrument for high tibial osteotomy," Acta Orthopaedica Scandinavica, vol. 60, No. 4, 1989, pp. 449-451.
Okuda et al., "Postoperative Incomplete Reduction of the Sesamoids as a Risk Factor for Recurrence of Hallux Valgus," The Journal of Bone and Joint Surgery, vol. 91-A, No. 1, Jul. 2009, pp. 1637-1645.
Osher et al., "Accurate Determination of Relative Metatarsal Protrusion with a Small Intermetatarsal Angle: A Novel Simplified Method," The Journal of Foot & Ankle Surgery, vol. 53, No. 5, Sep./Oct. 2014, published online: Jun. 3, 2014, pp. 548-556.
Otsuki et al., "Developing a novel custom cutting guide for curved per-acetabular osteotomy," International Orthopaedics (SICOT), vol. 37, 2013, pp. 1033-1038.
Patel et al., "Modified Lapidus Arthrodesis: Rate of Nonunion in 227 Cases," The Journal of Foot & Ankle Surgery, vol. 43, No. 1, Jan./Feb. 2004, pp. 37-42.
"Patient to Patient Precision, Accu-Cut, Osteotomy Guide System," BioPro, Foot & Ankle International Journal, vol. 23, No. 8, Aug. 2002, 2 pages.
Peters et al., "Flexor Hallucis Longus Tendon Laceration as a Complication of Total Ankle Arthroplasty," Foot & Ankle International, vol. 34, No. 1, 2013, pp. 148-149.
"Prophecy Inbone Preoperative Navigation Guides," Wright Medical Technology, Inc., Nov. 2013, 6 pages.
"RAYHACK Ulnar Shortening Generation II Low-Profile Locking System Surgical Technique," Wright Medical Technology, Inc., Dec. 2013, 20 pages.
Rx-Fix Mini Rail External Fixator, Wright Medical Technology, Brochure, Aug. 15, 2014, 2 pages.
Saltzman et al., "Prospective Controlled Trial of STAR Total Ankle Replacement Versus Ankle Fusion: Initial Results," Foot & Ankle International, vol. 30, No. 7, Jul. 2009, pp. 579-596.
Scanlan et al. "Technique Tip: Subtalar Joint Fusion Using a Parallel Guide and Double Screw Fixation," The Journal of Foot and Ankle Surgery, vol. 49, Issue 3, May-Jun. 2010, pp. 305-309, (Abstract Only).
Scranton Jr. et al., "Anatomic Variations in the First Ray: Part I. Anatomic Aspects Related to Bunion Surgery," Clinical Orthopaedics and Related Research, vol. 151, Sep. 1980, pp. 244-255.
Siddiqui et al. "Fixation Of Metatarsal Fracture With Bone Plate In A Dromedary Heifer," Open Veterinary Journal, vol. 3, No. 1, 2013, pp. 17-20.
Sidekick Stealth Rearfoot Fixator, Wright Medical Technology, Surgical Technique, Dec. 2, 2013, 20 pages.

(56) References Cited

OTHER PUBLICATIONS

Simpson et al., "Computer-Assisted Distraction Ostegogenesis By Ilizarov's Method," International Journal of Medical Robots and Computer Assisted Surgery, vol. 4, No. 4, Dec. 2008, pp. 310-320, (Abstract Only).
Small Bone External Fixation System, Acumed, Surgical Technique, Effective date Sep. 2014, 8 pages.
"Smith & Nephew scores a HAT-TRICK with its entry into the high-growth hammer toe repair market," Smith & Nephew, Jul. 31, 2014, 2 pages.
Stableloc External Fixation System, Acumed, Product Overview, Effective date Sep. 2015, 4 pages.
Stahl et al., "Derotation Of Post-Traumatic Femoral Deformities By Closed Intramedullary Sawing," Injury, vol. 37, No. 2, Feb. 2006, pp. 145-151, (Abstract Only).
Talbot et al.,"Assessing Sesamoid Subluxation: How Good is the AP Radiograph?," Foot and Ankle International, vol. 19, No. 8, Aug. 1998, pp. 547-554.
TempFix Spanning the Ankle Joint Half Pin and Transfixing Pin Techniques, Biomet Orthopedics, Surgical Technique, 2012, 16 pages.
Toth et al., "The Effect of First Ray Shortening in the Development of Metatarsalgia in the Second Through Fourth Rays After Metatarsal Osteotomy," Foot & Ankle International, vol. 28, No. 1, Jan. 2007, pp. 61-63.
Tricot et al., "3D-corrective osteotomy using surgical guides for posttraumatic distal humeral deformity," Acta Orthopaedica Belgica, vol. 78, No. 4, 2012, pp. 538-542.
Vitek et al., "Die Behandlung des Hallux rigidus mit Cheilektomie und Akin-Moberg-Osteotomie unter Verwendung einer neuen Schnittlehre und eines neuen Schraubensystems," Orthopadische Praxis, vol. 44, Nov. 2008, pp. 563-566, including English Abstract on p. 564.
Vitek, "Neue Techniken in der Fußchirurgie Das V-tek-System," ABW Wissenschaftsverlag GmbH, 2009, 11 pages, including English Abstract.
Weber et al., "A Simple System For Navigation Of Bone Alignment Osteotomies Of The Tibia," International Congress Series, vol. 1268, Jan. 2004, pp. 608-613, (Abstract Only).
Weil et al., "Anatomic Plantar Plate Repair Using the Weil Metatarsal Osteotomy Approach," Foot & Ankle Specialist, vol. 4, No. 3, 2011, pp. 145-150.
Wendl et al., "Navigation in der Knieendoprothetik," OP-Journal, vol. 17, 2002, pp. 22-27, including English Abstract.
Whipple et al., "Zimmer Herbert Whipple Bone Screw System: Surgical Techniques for Fixation of Scaphoid and Other Small Bone Fractures," Zimmer, 2003, 59 pages.
Yakacki et al. "Compression Forces of Internal and External Ankle Fixation Devices with Simulated Bone Resorption," Foot and Ankle International, vol. 31, No. 1, Jan. 2010, pp. 76-85, (Abstract Only).
"Accu-Cut Osteotomy Guide System," BioPro, Brochure, Oct. 2018, 2 pages.
"Acumed Osteotomiesystem Operationstechnik," Acumed, 2014, 19 pages (including 3 pages English translation).
Albano et al., "Biomechanical Study of Transcortical or Transtrabecular Bone Fixation of Patellar Tendon Graft wih Bioabsorbable Pins in ACL Reconstruction in Sheep," Revista Brasileira de Ortopedia (Rev Bras Ortop.) vol. 47, No. 1, 2012, pp. 43-49.
Alvine et al., "Peg and Dowel Fusion of the Proximal Interphalangeal Joint," Foot & Ankle, vol. 1, No. 2, 1980, pp. 90-94.
Anderson et al., "Uncemented STAR Total Ankle Prostheses," The Journal of Bone and Joint Surgery, vol. 86(1, Suppl 2), Sep. 2004, pp. 103-111, (Abstract Only).
Bednarz et al., "Modified Lapidus Procedure for the Treatment of Hypermobile Hallux Valgus," Foot & Ankle International, vol. 21, No. 10, Oct. 2000, pp. 816-821.
Blomer, "Knieendoprothetik—Herstellerische Probleme und technologische Entwicklungen," Orthopade, vol. 29, 2000, pp. 688-696, including English Abstract on p. 689.
Bouaicha et al., "Fixation of Maximal Shift Scarf Osteotomy with Inside-Out Plating: Technique Tip," Foot & Ankle International, vol. 32, No. 5, May 2011, pp. 567-569.
Carr et al., "Correctional Osteotomy for Metatarsus Primus Varus and Hallux Valgus," The Journal of Bone and Joint Surgery, vol. 50-A, No. 7, Oct. 1968, pp. 1353-1367.
Coetzee et al., "The Lapidus Procedure: A Prospective Cohort Outcome Study," Foot & Ankle International, vol. 25, No. 8, Aug. 2004, pp. 526-531.
Dayton et al., "Is Our Current Paradigm for Evaluation and Management of the Bunion Deformity Flawed? A Discussion of Procedure Philosophy Relative to Anatomy," The Journal of Foot and Ankle Surgery, vol. 54, 2015, pp. 102-111.
Dayton et al., "Observed Changes in Radiographic Measurements of the First Ray after Frontal and Transverse Plane Rotation of the Hallux: Does the Hallux Drive the Metatarsal in a Bunion Deformity? ," The Journal of Foot and Ankle Surgery, vol. 53, 2014, pp. 584-587.
Dayton et al., "Relationship Of Frontal Plane Rotation Of First Metatarsal To Proximal Articular Set Angle And Hallux Alignment In Patients Undergoing Tarsometatarsal Arthrodesis For Hallux Abducto Valgus: A Case Series And Critical Review Of The Literature," The Journal of Foot and Ankle Surgery, vol. 52, No. 3, May/Jun. 2013, pp. 348-354.
Dayton et al., "Quantitative Analysis of the Degree of Frontal Rotation Required to Anatomically Align the First Metatarsal Phalangeal Joint During Modified Tarsal-Metatarsal Arthrodesis Without Capsular Balancing," The Journal of Foot and Ankle Surgery, 2015, pp. 1-6.
De Geer et al., "A New Measure of Tibial Sesamoid Position in Hallux Valgus in Relation to the Coronal Rotation of the First Metatarsal in CT Scans," Foot and Ankle International, Mar. 26, 2015, 9 pages.
DiDomenico et al., "Correction of Frontal Plane Rotation of Sesamoid Apparatus during the Lapidus Procedure: A Novel Approach," The Journal of Foot and Ankle Surgery, vol. 53, 2014, pp. 248-251.
Dobbe et al. "Patient-Tailored Plate For Bone Fixation And Accurate 3D Positioning In Corrective Osteotomy," Medical and Biological Engineering and Computing, vol. 51, No. 1-2, Feb. 2013, pp. 19-27, (Abstract Only).
Doty et al., "Hallux valgus and hypermobility of the first ray: facts and fiction," International Orthopaedics, vol. 37, 2013, pp. 1655-1660.
EBI Extra Small Rail Fixator, Biomet Trauma, retrieved Dec. 19, 2014, from the Internet: <http://footandanklefixation.com/product/biomet-trauma-ebi-extra-small-rail-fixator>, 7 pages.
Dayton et al., "Comparison of the Mechanical Characteristics of a Universal Small Biplane Plating Technique Without Compression Screw and Single Anatomic Plate With Compression Screw," The Journal of Foot & Ankle Surgery, vol. 55, No. 3, May/Jun. 2016, published online: Feb. 9, 2016, pp. 567-571.
"Futura Forefoot Implant Arthroplasty Products," Tornier, Inc., 2008, 14 pages.
Galli et al., "Enhanced Lapidus Arthrodesis: Crossed Screw Technique With Middle Cuneiform Fixation Further Reduces Sagittal Mobility," The Journal of Foot & Ankle Surgery, vol. 54, vol. 3, May/Jun. 2015, published online: Nov. 21, 2014, pp. 437-440.
Garthwait, "Accu-Cut System Facilitates Enhanced Precision," Podiatry Today, vol. 18, No. 6, Jun. 2005, 6 pages.
Gonzalez Del Pino et al., "Variable Angle Locking Intercarpal Fusion System for Four-Corner Arthrodesis: Indications and Surgical Technique," Journal of Wrist Surgery, vol. 1, No. 1, Aug. 2012, pp. 73-78.
Gotte, "Entwicklung eines Assistenzrobotersystems für die Knieendoprothetik," Forschungsberichte, Technische Universitat Munchen, 165, 2002, 11 pages, including partial English Translation.
Gregg et al., "Plantar plate repair and Weil osteotomy for metatarsophalangeal joint instability," Foot and Ankle Surgery, vol. 13, 2007, pp. 116-121.

(56) References Cited

OTHER PUBLICATIONS

Grondal et al., “A Guide Plate for Accurate Positioning of First Metatarsophalangeal Joint during Fusion,” Operative Orthopädie Und Traumatologie, vol. 16, No. 2, 2004, pp. 167-178 (Abstract Only).
“Hat-Trick Lesser Toe Repair System,” Smith & Nephew, Brochure, Aug. 2014, 12 pages.
“Hat-Trick Lesser Toe Repair System, Foot and Ankle Technique Guide, Metatarsal Shortening Osteotomy Surgical Technique,” Smith & Nephew, 2014, 16 pages.
Hetherington et al., “Evaluation of surgical experience and the use of an osteotomy guide on the apical angle of an Austin osteotomy,” The Foot, vol. 18, 2008, pp. 159-164.
Hirao et al., “Computer assisted planning and custom-made surgical guide for malunited pronation deformity after first metatarsophalangeal joint arthrodesis in rheumatoid arthritis: A case report,” Computer Aided Surgery, vol. 19, Nos. 1-3, 2014, pp. 13-19.
“Hoffmann II Compact External Fixation System,” Stryker, Brochure, Literature No. 5075-1-500, 2006, 12 pages.
“Hoffmann II Micro Lengthener,” Stryker, Operative Technique, Literature No. 5075-2-002, 2008, 12 pages.
“Hoffmann Small System External Fixator Orthopedic Instruments,” Stryker, retrieved Dec. 19, 2014, from the Internet: <http://www.alibaba.com/product-detail/Stryker-Hoffmann-Small-System-External-Fixator_1438850129.html>, 3 pages.
Yasuda et al., “Proximal Supination Osteotomy of the First Metatarsal for Hallux Valgus,” Foot and Ankle International, vol. 36, No. 6, Jun. 2015, pp. 696-704.
Kim et al., “A New Measure of Tibial Sesamoid Position in Hallux Valgus in Relation to the Coronal Rotation of the First Metatarsal in CT Scans,” Foot and Ankle International, vol. 36, No. 8, 2015, pp. 944-952.
“Lag Screw Target Bow,” Stryker Leibinger GmbH & Co. KG, Germany 2004, 8 pages.
Lapidus, “The Author’s Bunion Operation From 1931 to 1959,” Clinical Orthopaedics, vol. 16, 1960, pp. 119-135.
Lieske et al., “Implantation einer Sprunggelenktotalendo-prothese vom Typ Salto 2,” Operative Orthopädie und Traumatologie, vol. 26, No. 4, 2014, pp. 401-413, including English Abstract on p. 403.
MAC (Multi Axial Correction) Fixation System, Biomet Trauma, retrieved Dec. 19, 2014, from the Internet: <http://footandanklefixation.com/product/biomet-trauma-mac-multi-axial-correction-fixation-system>, 7 pages.
Magin, “Computernavigierter Gelenkersatz am Knie mit dem Orthopilot,” Operative Orthopädie und Traumatologie, vol. 22, No. 1, 2010, pp. 63-80, including English Abstract on p. 64.
Magin, “Die belastungsstabile Lapidus-Arthrodese bei Hallux-valgus-Deformität mittels IVP-Plattenfixateur (V-TEK-System),” Operative Orthopädie und Traumatologie, vol. 26, No. 2, 2014, pp. 184-195, including English Abstract on p. 186.
Michelangelo Bunion System, Surgical Technique, Instratek Incorporated, publication date unknown, 4 pages.
Mini Joint Distractor, Arthrex, retrieved Dec. 19, 2014, from the Internet: <http://www.arthrex.com/foot-ankle/mini-joint-distractor/products>, 2 pages.
MiniRail System, Small Bone Innovations, Surgical Technique, 2010, 24 pages.
Miyake et al., “Three-Dimensional Corrective Osteotomy for Malunited Diaphyseal Forearm Fractures Using Custom-Made Surgical Guides Based on Computer Simulation,” JBJS Essential Surgical Techniques, vol. 2, No. 4, 2012, 11 pages.
Modular Rail System: External Fixator, Smith & Nephew, Surgical Technique, 2013, 44 pages.
Monnich et al., “A Hand Guided Robotic Planning System for Laser Osteotomy in Surgery,” World Congress on Medical Physics and Biomedical Engineering vol. 25/6: Surgery, Nimimal Invasive Interventions, Endoscopy and Image Guided Therapy, Sep. 7-12, 2009, pp. 59-62, (Abstract Only).
Moore et al., “Effect Of Ankle Flexion Angle On Axial Alignment Of Total Ankle Replacement,” Foot and Ankle International, vol. 31, No. 12, Dec. 2010, pp. 1093-1098, (Abstract Only).
Mortier et al., “Axial Rotation of the First Metatarsal Head in a Normal Population and Hallux Valgus Patients,” Orthopaedics and Traumatology: Surgery and Research, vol. 98, 2012, pp. 677-683.
Caldarella, “Lapidus Arthrodesis: Patient Selection and Surgical Technique”, Chapter 24, The Podiatry Institute, 1998, pp. 142-149.
Chambers, “The Frontal Plane Derotational Head Osteotomy for Correction of Valgus Rotation of the Hallux”, Chapter 52, The Podiatry Institute, 2004, pp. 301-307.
Cottom et al., “Fixation of Lapidus Arthrodesis with a Plantar Interfragmentary Screw and Medial Locking Plate: A Report of 88 Cases”, The Journal of Foot & Ankle Surgery 52, 2013, pp. 465-469.
Innomed, Inc, “Medial Malleolar / Bone Fragment Clamp”, Brochure, 2002, p. 1.
Lapidus, “Operative Correction of the Metatarsus Varus Primus in Hallux Valgus”, Sugery, Gynecology and Obstetrics, The Surgical Publishing Company of Chicago, Jan. 1934, p. 10.
McGlamry, “Lapidus XL: Gaining Stability Without Compromising Length”, Chapter 17, The Podiatry Institute, 2003, pp. 74-77.
OLMS, “The Modified Lapidus Arthrodesis for the Correction of the Hallux Valgus Deformity: Retrospective Analysis of 182 Cases”, Chapter 49, The Podiatry Institute, 2004, pp. 285-288.
Orthomed, Inc., “OrthoMed Bone Holding Instruments Product Catalog”, Section L, Available for download Nov. 2, 2013, p. 21.
Schuberth et al., “Minimally Invasive Lapidus Procedure”, Chapter 34, The Podiatry Institute, 2000, pp. 203-207.
Malay et al., “Instrumentation”, Chapter 1, McGlamry’s Comprehensive Textbook of Foot and Ankle Surgery, Fourth Edition, Published Wolters Kluwer Health Lippincott Williams & Wilkins, 2013, pp. 3-14.
Synthes, Inc, “Collinear Reduction Clamp—Handling Technique”, Synthes, Sep. 2008, p. 16.
Testa et al. “The Sesamoid Apparatus Position in Hallux Valgus Surgery”, Chapter 1, The Podiatry Institute, 2005, pp. 1-7.
Yu et al., “Hallux Valgus Surgery and the Sesamoid Apparatus”, Chapter 9, The Podiatry Institute, 1997, pp. 42-49.
Labib, “Lapidus Procedure for Hallux Valgus Correction with Mini TightRope”, Arthrex, Published Apr. 15, 2013, Retrieved from: https://www.arthrex.com/resources/VID1-0433-EN/lapidus-procedure-for-hallux-valgus-correction-with-mini-tightrope?referringteam=foot_and_ankle, Video captured Jul. 10, 2025, p. 4.
Defendant Stryker Corporation and Wright Medical Technology, Inc., Invalidity Contentions, No. 2:24-cv-09763-JKS-MAH, US District Court for the District of New Jersey, Aug. 4, 2025, 193 pages.
Downey et al., “Congenital Overlapping Fifth Toe Deformity”, Chapter 17, McGlamry’s Comprehensive Textbook of Foot and Ankle Surgery, Fourth Edition, Published Wolters Kluwer Health Lippincott Williams & Wilkins, 2013, pp. 154-164.
Dunn et al., “Tailor’s Bunion Deformity”, Chapter 23, McGlamry’s Comprehensive Textbook of Foot and Ankle Surgery, Fourth Edition, Published Wolters Kluwer Health Lippincott Williams & Wilkins, 2013, pp. 235-242.
DiDomenico et al., “Lapidus Bunionectomy”, Chapter 31, McGlamry’s Comprehensive Textbook of Foot and Ankle Surgery, Fourth Edition, Published Wolters Kluwer Health Lippincott Williams & Wilkins, 2013, pp. 322-330.
Vanore et al., “First Metatarsophalangeal Joint Arthroplasty”, Chapter 34, McGlamry’s Comprehensive Textbook of Foot and Ankle Surgery, Fourth Edition, Published Wolters Kluwer Health Lippincott Williams & Wilkins, 2013, pp. 362-399.
Claim Charts for Fishco Article, “Making the Lapidus Easy” The Podiatry Institute, Apr. 2014, Exhibit 1 of Defendant Stryker Corporation and Wright Medical Technology, Inc., Invalidity Contentions, No. 2:24-CV-09763-JKS-MAH, US District Court for the District of New Jersey, Aug. 4, 2025, 497 pages.
Claim Charts for McGlamry’s Book, “McGlamry’s Comprehensive Textbook of Foot and Ankle Surgery”, 4th ed., vol. 1, Published 2013, Exhibit 2 of Defendant Stryker Corporation and Wright

(56) References Cited

OTHER PUBLICATIONS

Medical Technology, Inc., Invalidity Contentions, No. 2:24-CV-09763-JKS-MAH, US District Court for the District of New Jersey, Aug. 4, 2025, 535 pages.
Claim Charts for Cottom Article, " Fixation of Lapidus Arthrodesis with a Plantar Interfragmentary Screw and Medial Locking Plate: A Report of 88 Cases" The Journal of Foot & Ankle Surgery, vol. 52, pp. 465-469, Exhibit 3 of Defendant Stryker Corporation and Wright Medical Technology, Inc., Invalidity Contentions, No. 2:24-CV-09763-JKS-MAH, US District Court for the District of New Jersey, Aug. 4, 2025, 639 pages.
Claim Charts for Arthrex Labib Video, " Lapidus Procedure for Hallux Valgus Correction with Mini TightRope", Arthrex.com, was published on Apr. 15, 2013, Exhibit 4 of Defendant Stryker Corporation and Wright Medical Technology, Inc., Invalidity Contentions, No. 2:24-CV-09763-JKS-MAH, US District Court for the District of New Jersey, Aug. 4, 2025, 579 pages.
Claim Charts for U.S. Pat. No. 8,313,492 ("Wong"), "Drill Guide Assembly", Provisional Application Filed May 29, 2009, Issued Nov. 20, 2012, Exhibit 5 of Defendant Stryker Corporation and Wright Medical Technology, Inc., Invalidity Contentions, No. 2:24-CV-09763-JKS-MAH, US District Court for the District of New Jersey, Aug. 4, 2025, 964 pages.
Claim Chart for U.S. Publication No. 2016/0213384 ("Fallin"), "Freeform Tri-Planar Osteotomy Guide and Method", Provisional Application Filed Dec. 4, 2015, Exhibit 6 of Defendant Stryker Corporation and Wright Medical Technology, Inc., Invalidity Contentions, No. 2:24-CV-09763-JKS-MAH, US District Court for the District of New Jersey, Aug. 4, 2025, 168 pages.
Claim Chart for McGlamry's Book, " McGlamry's Comprehensive Textbook of Foot and Ankle Surgery", 4th ed., vol. 1, Published 2013, Exhibit 7 of Defendant Stryker Corporation and Wright Medical Technology, Inc., Invalidity Contentions, No. 2:24-CV-09763-JKS-MAH, US District Court for the District of New Jersey, Aug. 4, 2025, 234 pages.
Claim Chart for Fishco Article, "Making the Lapidus Easy," The Podiatry Institute, Apr. 2014, Exhibit 8 of Defendant Stryker Corporation and Wright Medical Technology, Inc., Invalidity Contentions, No. 2:24-CV-09763-JKS-MAH, US District Court for the District of New Jersey, Aug. 4, 2025, 250 pages.
Claim Chart for Arthrex Labib Video, " Lapidus Procedure for Hallux Valgus Correction with Mini TightRope", Arthrex.com, was published on Apr. 15, 2013, Exhibit 9 of Defendant Stryker Corporation and Wright Medical Technology, Inc., Invalidity Contentions, No. 2:24-CV-09763-JKS-MAH, US District Court for the District of New Jersey, Aug. 4, 2025, 215 pages.
Baravarian et al., "Lapidus Bunionectomy: arthrodesis of the first metatarsocunieform joint", Clin Podiatr Surg, 21, 2004, pp. 97-111.
Dunn et al., "Principles of Arthrodesis", Chapter 55, McGlamrys Comprehensive Textbook of Foot and Ankle Surgery, Fourth Edition, Published Wolters Kluwer Health Lippincott Williams & Wilkins, 2013, pp. 803-809.
Hofbauer et al., "The Lapidus Procedure", Clinics in Podiatric Medicine and Surgery, vol. 13, No. 3, Jul. 1996, pp. 485-496.
Judge, "Complications in Hallux Abducto Valgus Surgery (Excluding Hallux Varus)", Chapter 36, McGlamrys Comprehensive Textbook of Foot and Ankle Surgery, Fourth Edition, Published Wolters Kluwer Health Lippincott Williams & Wilkins, 2013, pp. 417-460.
Mothershed, "Principles of Arthrodesis", Chapter 16, Part 1 & 2, McGlamrys Comprehensive Textbook of Foot and Ankle Surgery, Third Edition, Published Wolters Kluwer Health Lippincott Williams & Wilkins, 2004, pp. 529-556.
Okuda et al., "Proximal abduction-supination osteotomy of the first metatarsal for adolescent hallux valgus: a preliminary report", J Orthop Sci, 18, Published Mar. 20, 2013, pp. 419-425.
Franssen et al., "One Century of Kirschner wires and Kirschner wire insertion techniques: A historical review", Acta Orthopaedica Belgica, vol. 76, pp. 1-6.
Paragon 28, "Surgical Technique Guide Bun-Yo-Matic Lapidus Clamp System", Apr. 25, 2025, p. 32.
Schmid et al., "The Modified Lapidus Fusion", Foot Ankle Clin N Am, 19, 2014, pp. 223-233.
Toolan, "Surgical Strategies: The Lapidus Procedure", Foot & Ankle International, vol. 28, No. 10, Oct. 2007, pp. 1108-1114.
Young et al., "New Techniques and Alternative Fixation for the Lapidus Arthrodesis", Clin Podiatr Med Surg, 30, 2013, pp. 423-434.
Paragon 28, Inc., "Petition for Inter Partes Review of U.S. Pat. No. 12,102,368", *Paragon 28, Inc.* Petitioner v. *Treace Medical Concepts Inc.* Patent Owner, Case IPR2026-00194, Filed Jan. 5, 2026, p. 114.
"Declaration of Dr. Steven K. Neufeld, MD, in Support of Petition for Inter Partes Review of U.S. Pat. No. 12,102,368", *Paaragon 28, Inc.* Petitioner v. *Treace Medical Concepts Inc.* Patent Owner, Case IPR2026-00194, Executed Dec 31, 2025, p. 142.
Paragon 28, Inc., "Petition for Post-Grant Review of U.S. Pat. No. 12,268,397", *Paragon 28, Inc.* Petitioner v. *Treace Medical Concepts Inc.* Patent Owner, Case PGR2026-00017, Filed Dec 19, 2025, p. 126.
"Declaration of Dr. Steven K. Neufeld, MD, in Support of Petition for Post-Grant Review of U.S. Pat. No. 12,268,397", *Paragon 28, Inc.* Petitioner v. *Treace Medical Concepts Inc.* Patent Owner, Case PGR2026-00017, Executed Dec 18, 2025, p. 104.
Paragon 28, Inc, "Petition for Post Grant Review of U.S. Pat. No. 12,268,428", *Paragon 28, Inc.* Petitioner v. *Treace Medical Concepts Inc.* Patent Owner, Case PGR2026-00020, Filed Dec 23, 2025, p. 148.
"Declaration of Dr. Steven K. Neufeld, MD, in Support of Petition for Post-Grant Review of U.S. Pat. No. 12,268,428", *Paragon 28, Inc.* Petitioner v. *Treace Medical Concepts Inc.* Patent Owner, Case PGR2026-00020, Executed Dec 23, 2025, p. 155.
Paragon 28, Inc, "Petition for Post-Grant Review of U.S. Pat. No. 12,274,481", *Paragon 28, Inc.* Petitioner v. *Treace Medical Concepts Inc.* Patent Owner, Case PGR2026-00022, Filed Jan. 13, 2026, p. 138.
"Declaration of Dr. Steven K. Neufeld, MD, in Support of Petition for Post-Grant Review of U.S. Pat. No. 12,274,481", *Paragon 28, Inc.* Petitioner v. *Treace Medical Concepts Inc.* Patent Owner, Case PGR2026-00022, Executed Jan. 13, 2026, p. 179.
Paragon 28, Inc., "Petition for Post-Grant Review of U.S. Pat. No. 12,349,941", *Paragon 28, Inc.* Petitioner v. *Treace Medical Concepts Inc.* Patent Owner, Case PGR2026-00031, Filed Mar. 3, 2026, p. 137.
"Declaration of Dr. Steven K. Neufeld, MD, in Support of Petition for Post-Grant Review of U.S. Pat. No. 12,349,941", *Paragon 28, Inc.* Petitioner v. *Treace Medical Concepts Inc.* Patent Owner, Case PGR2026-00031, Executed Mar. 3, 2026, p. 172.
Treace Medical Concepts, Inc., "Patent Owner's Preliminary Response", *Paragon 28, Inc.* Petitioner v. *Treace Medical Concepts Inc.* Patent Owner, Case PGR2026-00017, U.S. Pat. No. 12,268,397, Filed Apr. 1, 2026, p. 69.
Treace Medical Concepts, Inc., "Patent Owner's Preliminary Response", *Paragon 28, Inc.* Petitioner v. *Treace Medical Concepts Inc.* Patent Owner, Case PGR2026-00020, U.S. Pat. No. 12,268,428, Filed Apr. 6, 2026, p. 33.
Treace Medical Concepts, Inc., "Patent Owner's Preliminary Response", *Paragon 28, Inc.* Petitioner v. *Treace Medical Concepts Inc.* Patent Owner, Case PGR2026-00194, U.S. Pat. No. 12,102,368, Filed Apr. 13, 2026, p. 51.
Treace Medical Concepts, Inc., "Patent Owner's Preliminary Response", *Paragon 28, Inc.* Petitioner v. *Treace Medical Concepts Inc.* Patent Owner, Case PGR2026-00022, U.S. Pat. No. 12,274,481, Filed Apr. 22, 2026, p. 42.
"Declaration of Michelle L. Warmath and English Translation of European Patent Application EP 1508316 A1", dated Nov. 22, 2025, p. 59.
"Declaration of Daniel C. Farber, MD, in Support of the Patent Owner's Preliminary Response", *Paragon 28, Inc.* Petitioner v. *Treace Medical Concepts Inc.* Patent Owner, Case PGR2026-00017, U.S. Pat. No. 12,268,397, Executed Mar. 31, 2026, p. 18.
"Declaration of Daniel C. Farber, MD, in Support of the Patent Owner's Preliminary Response", *Paragon 28, Inc.* Petitioner v.

(56) References Cited

OTHER PUBLICATIONS

*Treace Medical Concepts Inc.* Patent Owner, Case PGR2026-00020, U.S. Pat. No. 12,268,428, Executed Mar. 31, 2026, p. 8.
"Declaration of Daniel C. Farber, MD, in Support of the Patent Owner's Preliminary Response", *Paragon 28, Inc.* Petitioner v. *Treace Medical Concepts Inc.* Patent Owner, Case PGR2026-00194, U.S. Pat. No. 12,102,368, Executed Apr. 10, 2026, p. 18.
"Declaration of Daniel C. Farber, MD, in Support of the Patent Owner's Preliminary Response", *Paragon 28, Inc.* Petitioner v. *Treace Medical Concepts Inc.* Patent Owner, Case PGR2026-00022, U.S. Pat. No. 12,274,481, Executed Apr. 15, 2026, p. 15.

* cited by examiner

BONE CUTTING GUIDE SYSTEMS AND METHODS

RELATED APPLICATION

This application is a continuation of U.S. patent application Ser. No. 17/106,306, filed Nov. 30, 2020, which is a continuation of U.S. patent application Ser. No. 15/210,497, filed Jul. 14, 2016 and issued as U.S. Pat. No. 10,849,663 on Dec. 1, 2020, which claims the benefit of U.S. Provisional Application Ser. No. 62/192,290, filed Jul. 14, 2015. The entire contents of these applications are hereby incorporated by reference.

TECHNICAL FIELD

This disclosure relates generally to devices and methods for cutting bones.

BACKGROUND

Bones, such as the bones of a foot, may be anatomically misaligned. In certain circumstances, surgical intervention is required to correctly align the bones to reduce patient discomfort and improve patient quality of life.

SUMMARY

In general, this disclosure is directed to bone cutting guide systems and techniques for cutting bones. In some examples, a bone cutting guide includes a support that houses a shaft that can translate relative to the support. The shaft may carry a main guide member that defines one or more cutting guide surfaces. For example, the main guide member may define opposed guide surfaces configured to receive a cutting member. In use, the cutting member may be inserted between the opposed guide surfaces and bounded within a range of movement by the guide surfaces, causing the cutting member to be directed at a cutting location under the guide surfaces. Additionally or alternatively, the main guide member may define a single cutting surface/plane. The cutting surface/plane may be a surface against which a clinician can position a cutting member and then guide the cutting member along the cutting surface/plane to perform a cutting operation.

In some configurations, the bone cutting guide includes fixation members, such as fixation pins or apertures, that allow the main body to be fixated on or adjacent a bone to be cut. For example, in use, a clinician may fixate the main body to a bone (e.g., a first metatarsal). Thereafter, the clinician may translate the main guide member having at least one cutting guide surface (e.g., opposed cutting guide surfaces) relative to the fixed main body. The clinician can translate the main guide member by sliding or rotating the shaft housed within the main body, e.g., causing the distal end of the shaft and main guide member carried thereon away from or towards the main body. Once suitably positioned, the clinician may or may not lock the location of the shaft and perform one or more cuts through the guide surfaces of the main guide member.

To perform a surgical procedure, a clinician may attach the support of the bone cutting guide to a bone. For example, the clinician may insert fixation members, such as fixation pins or screws, through apertures in the support to fixate the support to the bone (e.g., first metatarsal). Thereafter, the clinician may translate the main guide member having at least one cutting guide surface (e.g., opposed cutting guide surfaces) relative to the support. The clinician can translate the main guide member by moving a shaft housed within the inner cavity of the support, e.g., causing the distal end of the shaft and main guide member carried thereon to move away from or towards the support. Once suitably positioned, the clinician may or may not lock the location of the shaft and perform one or more cuts through the guide surfaces of the main guide member.

The details of one or more examples are set forth in the accompanying drawings and the description below. Other features, objects, and advantages will be apparent from the description and drawings, and from the claims.

DETAILED DESCRIPTION

Figure 1:
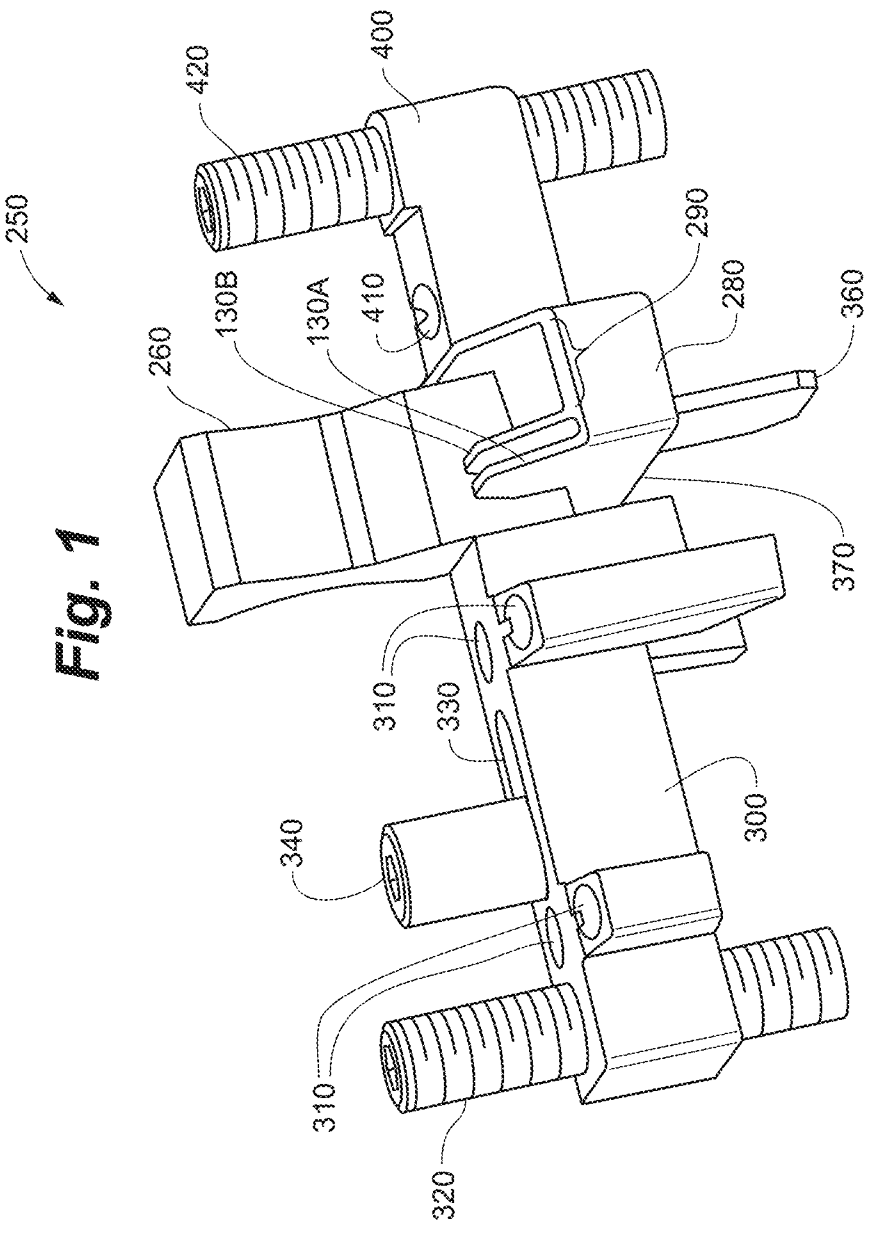
FIG. 1 is a perspective view of a bone cutting guide in accordance with an embodiment of the invention.

The following detailed description is exemplary in nature and is not intended to limit the scope, applicability, or configuration of the invention in any way. Rather, the following description provides some practical illustrations for implementing exemplary embodiments of the present invention. Examples of constructions, materials, and dimensions are provided for selected elements, and all other elements employ that which is known to those of ordinary skill in the field of the invention. Those skilled in the art will recognize that many of the noted examples have a variety of suitable alternatives.

Embodiments of the present invention include a bone cutting guide. In an exemplary application, embodiments of the bone cutting guide can be useful during a surgical procedure, such as a bone alignment, osteotomy, fusion procedure, and/or other procedures where one or more bones are to be cut. Such a procedure can be performed, for example, on bones (e.g., adjacent bones separated by a joint or different portions of a single bone) in the foot or hand, where bones are relatively smaller compared to bones in other parts of the human anatomy. In one example, a procedure utilizing the bone cutting guide can be performed to correct an alignment between a metatarsal (e.g. a first metatarsal) and a cuneiform (e.g., a first cuneiform), such as a bunion correction. An example of such a procedure is a Lapidus procedure. In another example, the procedure can be performed by modifying an alignment of a metatarsal (e.g. a first metatarsal). An example of such a procedure is a basilar metatarsal osteotomy procedure.

FIGS. 1-4 show an embodiment of a bone cutting guide 250. The bone cutting guide 250 includes a support 300 that defines an inner cavity. In one embodiment, the support 300 includes at least one fixation aperture 310 to receive at least one fixation pin. As shown, fixation apertures 310 can extend through the support 300 at a vertical angle (e.g., parallel to the longitudinal axis of the support) or a skewed angle relative to the longitudinal axis of the support (e.g., an angle ranging from 10 degrees to 55 degrees relative to the longitudinal axis of the support, such as an angle of approximately 20 degrees). In some configurations, the bone cutting guide 250 also includes an adjustable stabilization screw 320 engaged with the support 300 that can be used to stabilize the support with respect to a bone.

In the configuration of FIGS. 1-4, the bone cutting guide 250 includes a slot 330 and a securing component 340. The slot 330 is formed on and/or through at least a portion of a surface of the support 300. The securing component 340 is positioned at least partially within the slot 330 and configured to translate along the slot relative to the support 300. For example, the securing component 340 can have a first end with a diameter greater than a diameter of a second opposite end, such that the first end of the securing component 340 is supported by the slot 330 (e.g., the first end has a diameter greater than a width of the slot) while the second end of the securing component 340 is positioned within the slot (e.g., the second end has a diameter less than a width of the slot).

Figure 2:
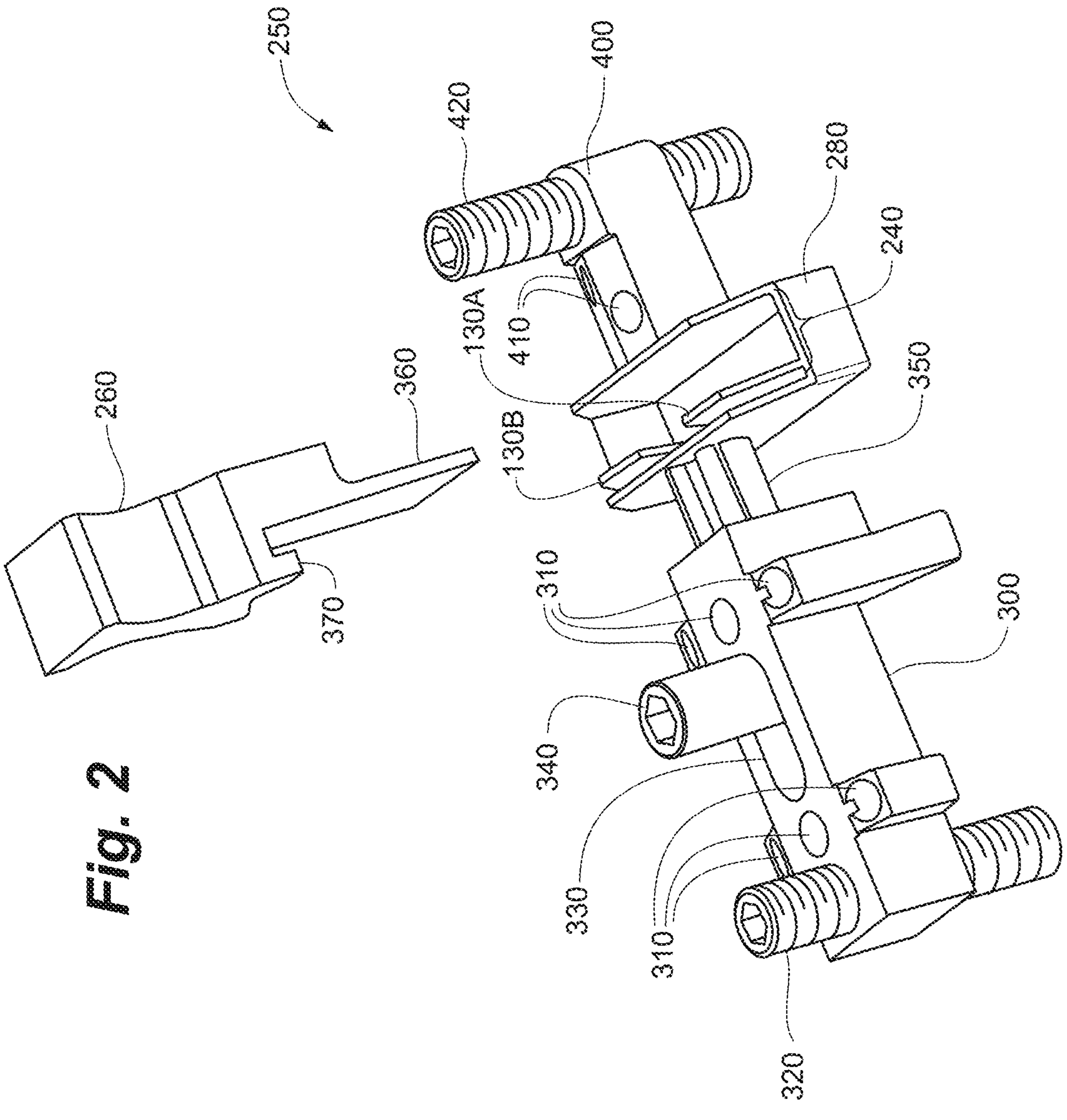
FIG. 2 is a perspective view of the bone cutting guide of FIG. 1, with a spacer detached.
Figure 3:
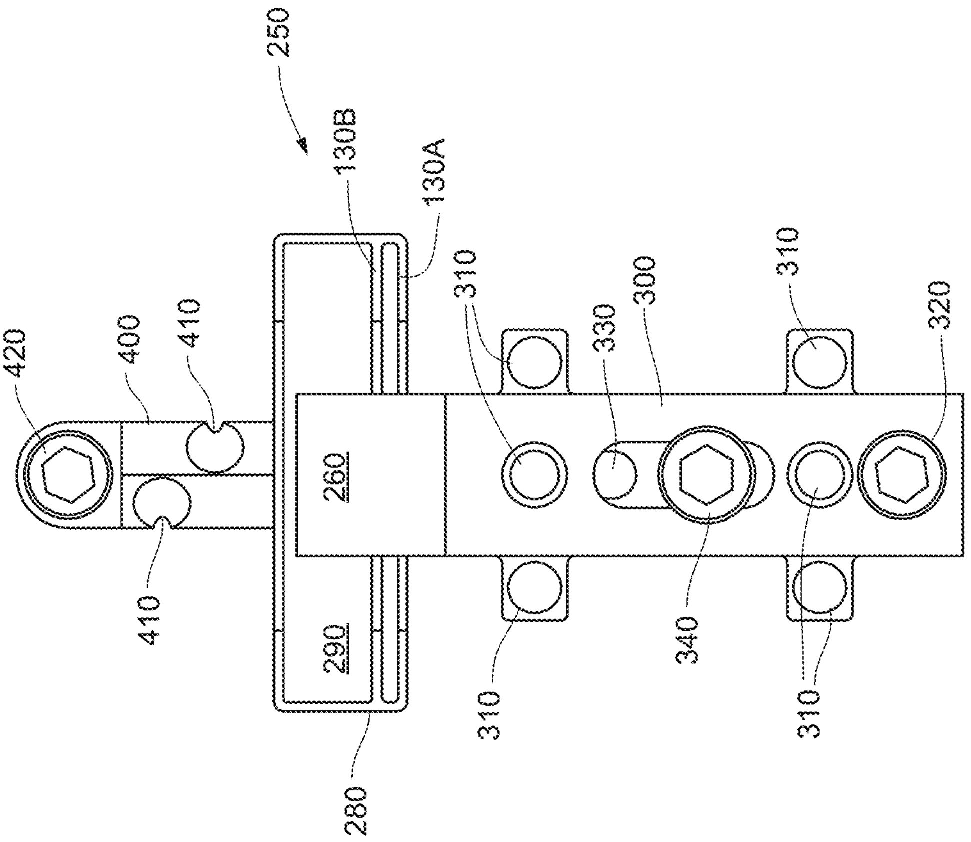
FIG. 3 is a top view of the bone cutting guide of FIG. 1.
Figure 4:
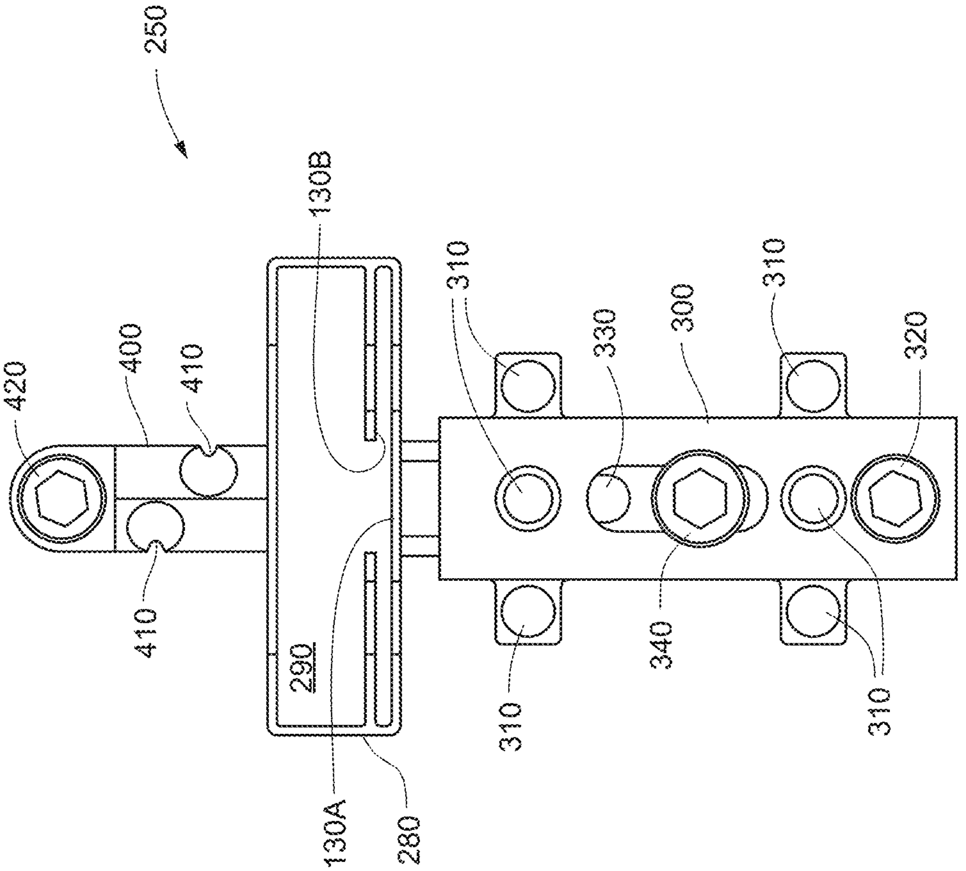
FIG. 4 is a top view of the bone cutting guide of FIG. 1, with the spacer removed.

As shown best in FIG. 2, a shaft 350 can be positioned at least partially within the inner cavity of the support 300. The shaft 350 can be configured to translate within the inner cavity relative to the support 300, such that the shaft can project out from the inner cavity and retract into the inner cavity (compare shaft position in FIG. 1 to FIG. 2). In one embodiment, the securing component 340 can be threadingly engaged with the support 300 to bear against the shaft 350 to prevent the shaft 350 from traveling with the cavity when desired.

The bone cutting guide 250 in the illustrate example includes a main guide member 280 disposed on the shaft 350. In some embodiments, the main guide member 280 can be integral with the shaft, while in other embodiments the main guide member and the shaft can be separate components coupled together. The main guide member 280 can have a first guide surface 130A and, optionally, a second guide surface 130B. The first and second guide surfaces 130A and 130B can be adjacent surfaces facing one another with a space defined between the first and second guide surfaces 130A and 130B. In use, a clinician can position a cutting member (e.g., a saw) against first guide surface 130A (e.g., between first and second guide surfaces 130A and 130B) and translate the cutting member along or through the guide surface(s). In this way, the guide surface(s) can align the cutting member with the surface of a bone to be cut.

In the illustrated embodiment, the second guide surface 130B contains a gap bisecting the planar face of the second guide surface, such that the second guide surface 130B is not a single, continuous surface. This gap can be used by the clinician to visualize the cutting member when positioned between the first and second guide surfaces 130A and 130B. In other embodiments, the second guide surface 130B can be a single, continuous surface lacking any such gap.

As shown in FIGS. 1 and 2, the first guide surface 130A may define a first plane while the second guide surface 130B may define a second plane. The first guide surface 130A and the second guide surface 130B can be arranged such that the first plane is parallel to the second plane, with the space therebetween, as shown in FIGS. 1 and 2. Alternatively, the guide surfaces can be arranged such that the first and/or second planes are skewed (e.g., non-parallel relative to each other). Additionally, in some embodiments, the main guide member 280 includes a viewing window 290 to provide a visual path to bones during cuts.

In the embodiment shown in FIGS. 1 and 2, the cutting guide 250 includes a removable spacer 260 engageable with the main guide member 280. The spacer 260 can have a first portion 360 configured to extend into a joint space (e.g., in a joint space between a first metatarsal and medial cuneiform) and a second portion 370 engageable with the main guide member 280. Such a spacer can be useful for positioning the main cut guide at a desired position with respect to a joint. Further, the first and second surfaces of the main cut guide and/or the surfaces of the spacer can be used to establish a pre-determined cut thickness.

Some embodiments of the cutting guide 250 include an anchor 400 to connect to a bone portion that is spaced from a bone portion to which the support 300 is connected. For example, cutting guide 250 may bridge a joint, fracture, or cut with the adjustable stabilization screw 320 positioned on one bone portion (e.g., a metatarsal or cuneiform) and the anchor positioned on the opposite side (e.g., the other of the metatarsal or cuneiform). In some embodiments, the anchor 400 is translatable with the shaft 350 and located along the shaft 350 on a side of the main guide member 280 opposite the support 300.

In one embodiment, the anchor 400 includes at least one fixation aperture 410 to receive at least one fixation pin. Such aperture(s) may extend through the anchor at a parallel (e.g., vertical) or skewed angle relative to the longitudinal axis of the anchor. Further, as shown, a second adjustable stabilization screw 420 can be provided to stabilize the anchor with respect to a bone. In some embodiments, after making an angular correction to a bone, the anchor 400 can be used to hold the angular orientation of the bone so that a second cut can be made parallel to the first cut.

In practice, the bone cutting guide 250 can be used to guide one or more cutting operations performed on a bone or bones. For example, the bone cutting guide 250 can be used to cut the end faces of adjacent bones to prepare the end faces (e.g., leading edges) of the bones. Such adjacent end faces can end faces of two different bones separated by a joint, or can be different portions of a single bone, separated by a fracture. In some embodiments, a clinician may attach the bone cutting guide 250 to the bone or bones to be cut then advance a cutting member along one or more guide surfaces of the bone cutting guide to cut the end faces of the one or more bones. The clinician may realign the bones relative to each other before or after the bones are cut and may also perform additional surgical steps, such as bone plating, after the cuts have been made.

Figure 5:
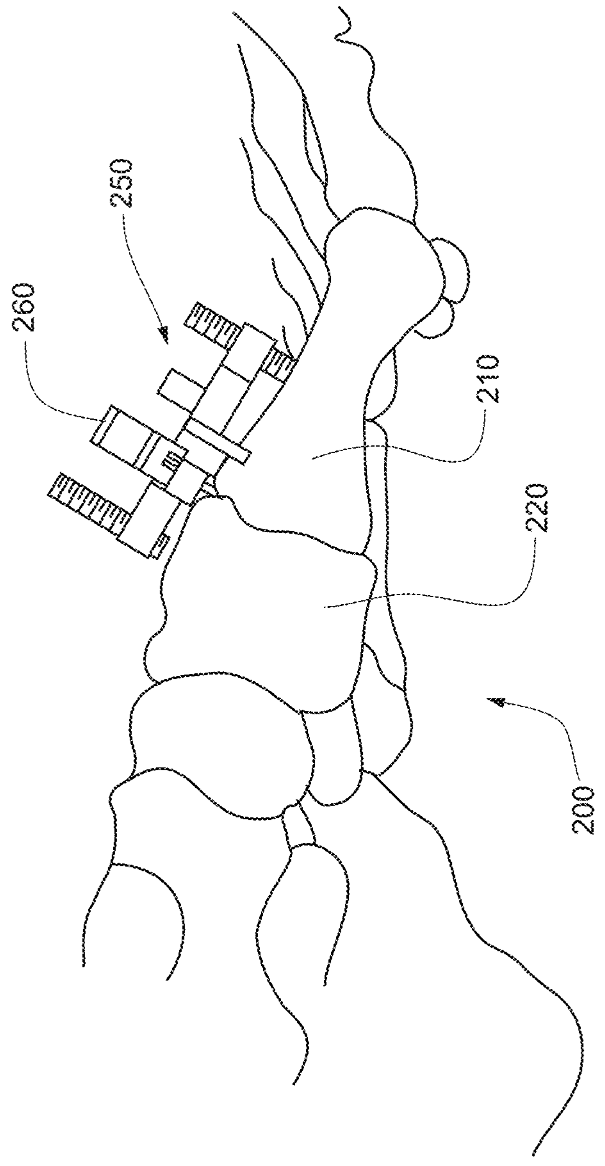
FIG. 5 is a side perspective view of a bone cutting guide on a foot in accordance with a medical procedure of an exemplary embodiment of the invention.
Figure 6:
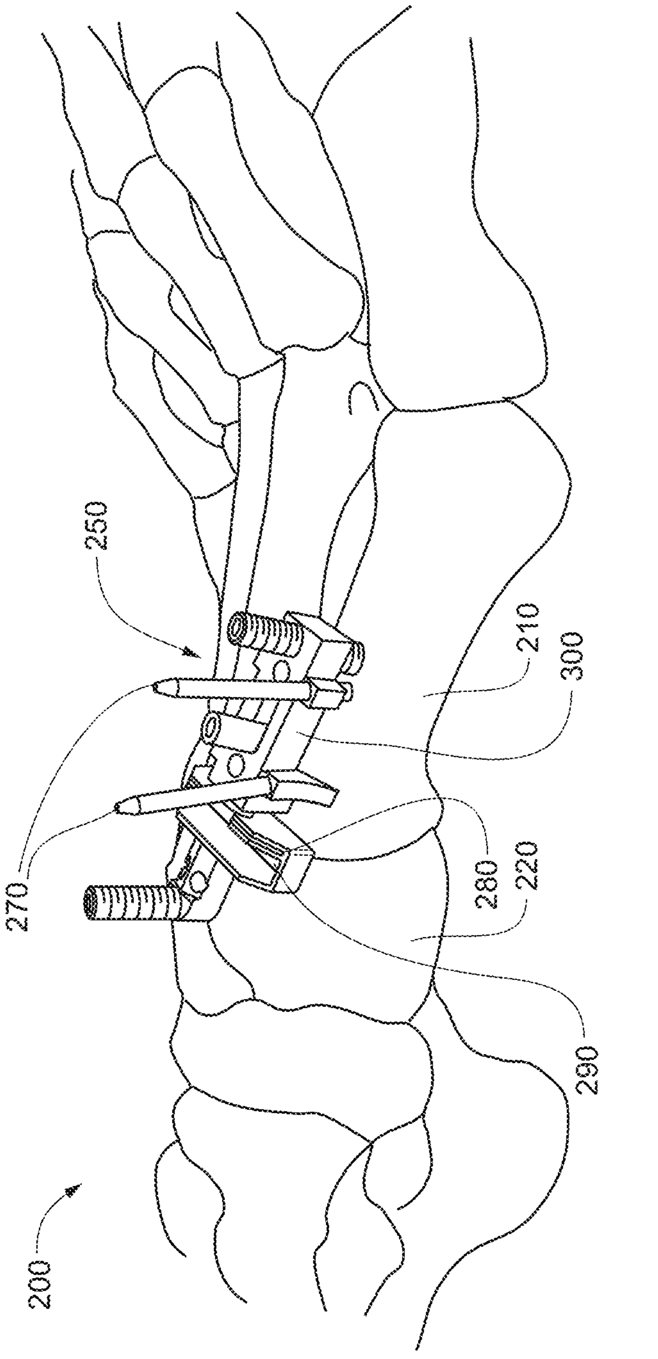
FIG. 6 is a side perspective view of a bone cutting guide on a foot held by fixation pins and positioned for a first bone cut in accordance with an embodiment of the invention.
Figure 7:
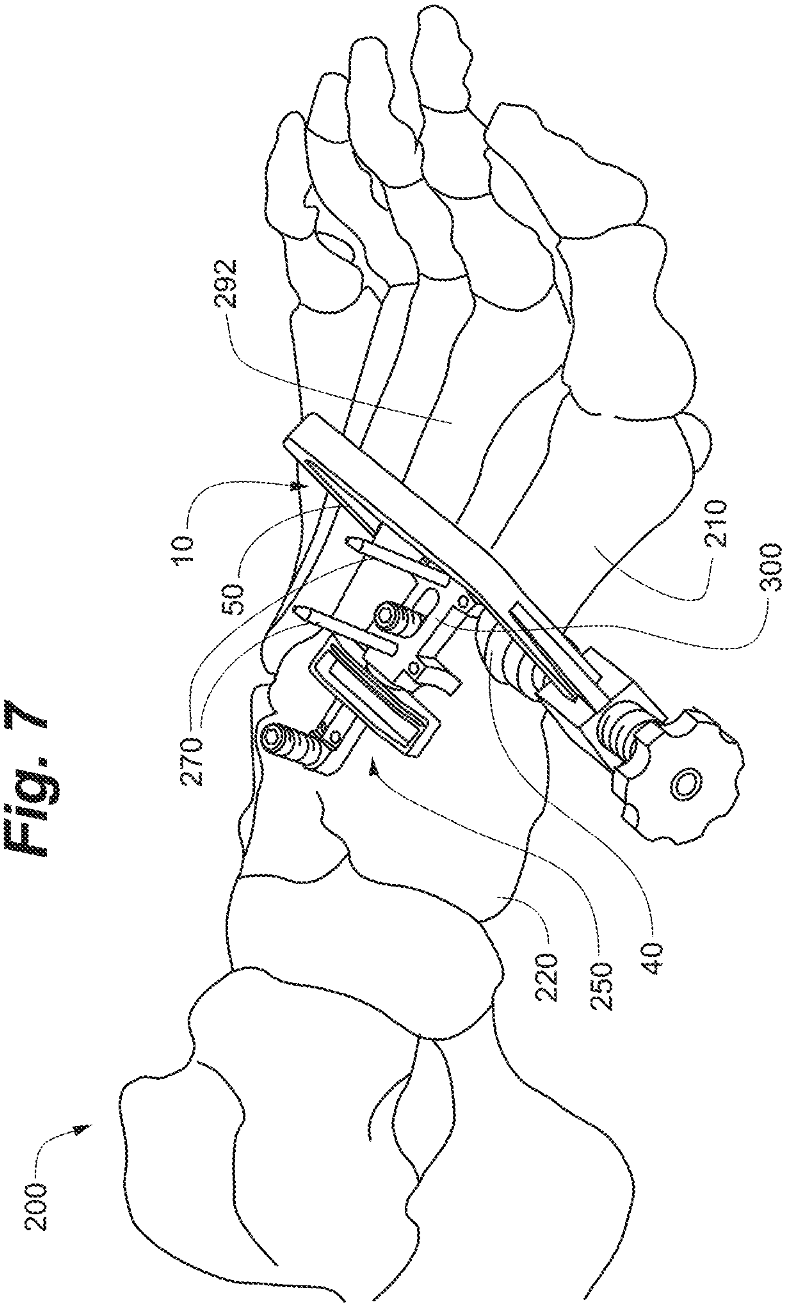
FIG. 7 is a perspective view of a bone cutting guide and a bone positioning guide on a foot in accordance with an embodiment of the invention.

FIGS. 5-13 illustrate steps of an exemplary method for cutting a bone using a bone cutting guide, such as bone cutting guide 250 described with respect to FIGS. 1-4, during a medical procedure. FIGS. 5-13 depict a foot 200 having a first metatarsal 210 and a first cuneiform 220 (medial cuneiform). In FIG. 5, the bone cutting guide 250 is positioned in longitudinal alignment with the long axis of the first metatarsal 210 and the first cuneiform 220, generally on the dorsal or dorsal-medial surface. As shown, the spacer 260 can be positioned within the joint between the first metatarsal and the first cuneiform. As shown in FIG. 6, fixation pins 270 can be inserted into the support 300 of the bone cutting guide 250 through angled apertures to fix the position of the cutting guide 250 to the first metatarsal 210 and the spacer can be removed. The end of the first metatarsal 210 facing the first cuneiform 220 can be cut with a cutting member (e.g., saw) inserted through the main guide member 280 having parallel first and second surfaces. The main guide member can also include a viewing window 290 adjacent the first and second surfaces to facilitate visualization of the cutting procedure by the clinician. The cutting guide 250 can be removed vertically from the fixation pins 270 and the bone slice removed. As shown in FIG. 7, the cutting guide 250 can be inserted back on the foot 200, such as by inserting the fixation pins 270 through vertical apertures in support 300.

Figure 8:
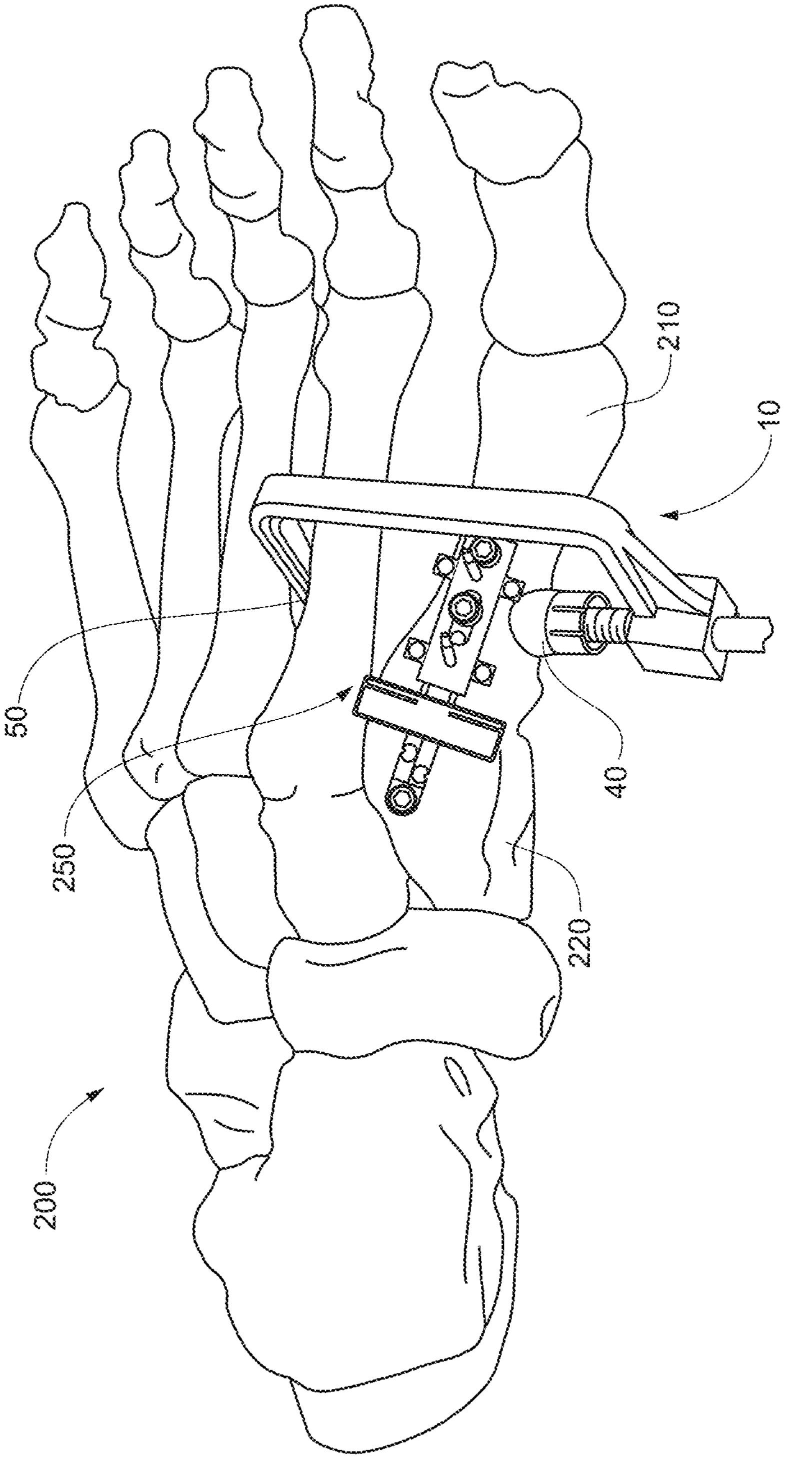
FIG. 8 is a perspective view of a bone cutting guide and a bone positioning guide on a foot depicting a bone adjustment in accordance with an embodiment of the invention.
Figure 9:
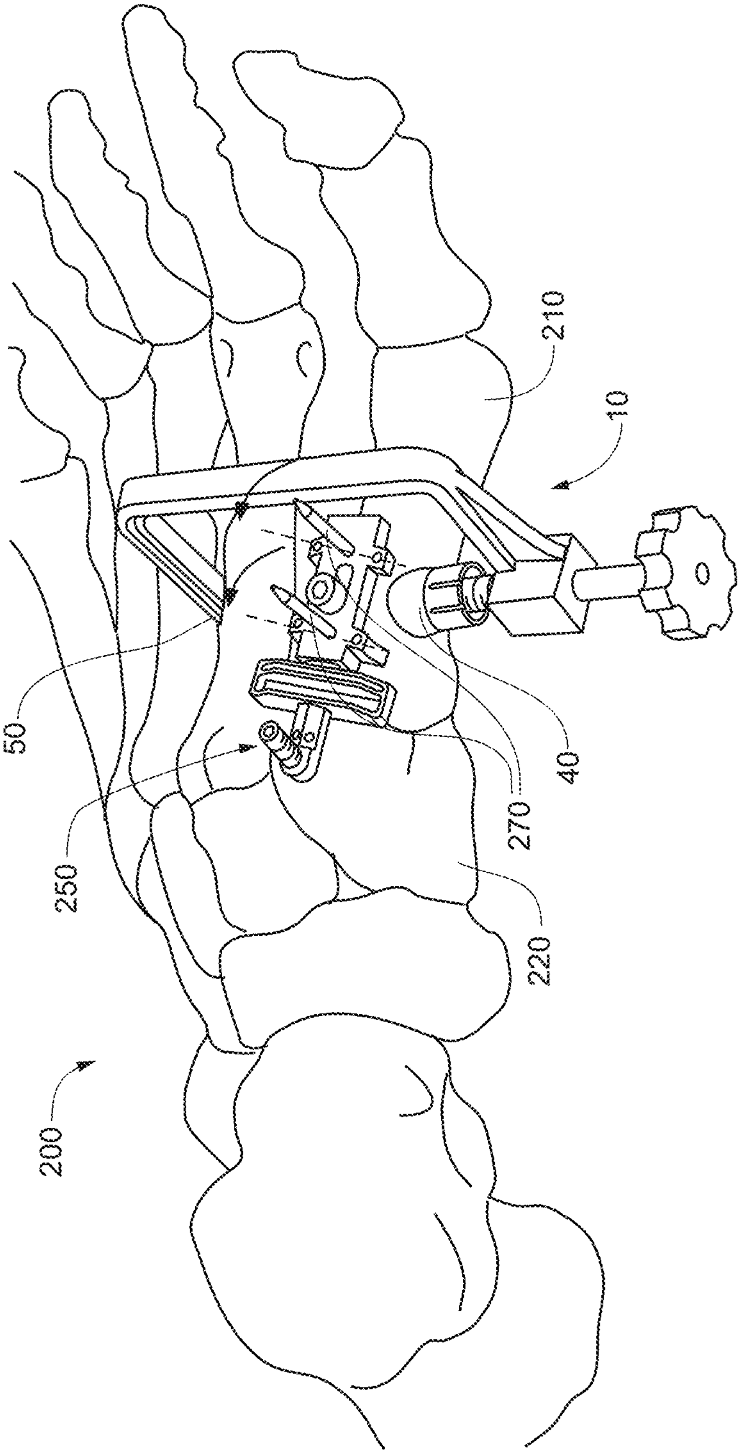
FIG. 9 is a perspective view of a bone cutting guide and a bone positioning guide on a foot depicting a bone adjustment in accordance with an embodiment of the invention.

Also shown in FIG. 7, a bone positioning guide 10 can be attached to the first metatarsal 210 and adjacent second metatarsal 292 (e.g., by installing the bone positioning guide over the top of the cutting guide 250). In some examples, a concave surface of a bone engagement member 40 can be placed in apposition to a medial surface of the first metatarsal 210 and a tip 50 can be placed in apposition to a lateral side of a different metatarsal, such as a second metatarsal 292. FIG. 8 shows repositioning of the first metatarsal 210 with respect to the second metatarsal 292 by moving the bone engagement member 40 with respect to the tip 50 to correct a transverse plane deformity. FIG. 9 shows rotation of the first metatarsal 210 with respect to the bone engagement member 40 to correct a frontal plane deformity. In some embodiments, the fixation pins 270 can be used to impart rotational force to the first metatarsal 210, e.g., by the clinician grasping one or more of the pins and using the pins to physically manipulate the position of the first metatarsal 210. The bone positioning guide 10 can hold the desired position of the first metatarsal.

Figure 10:
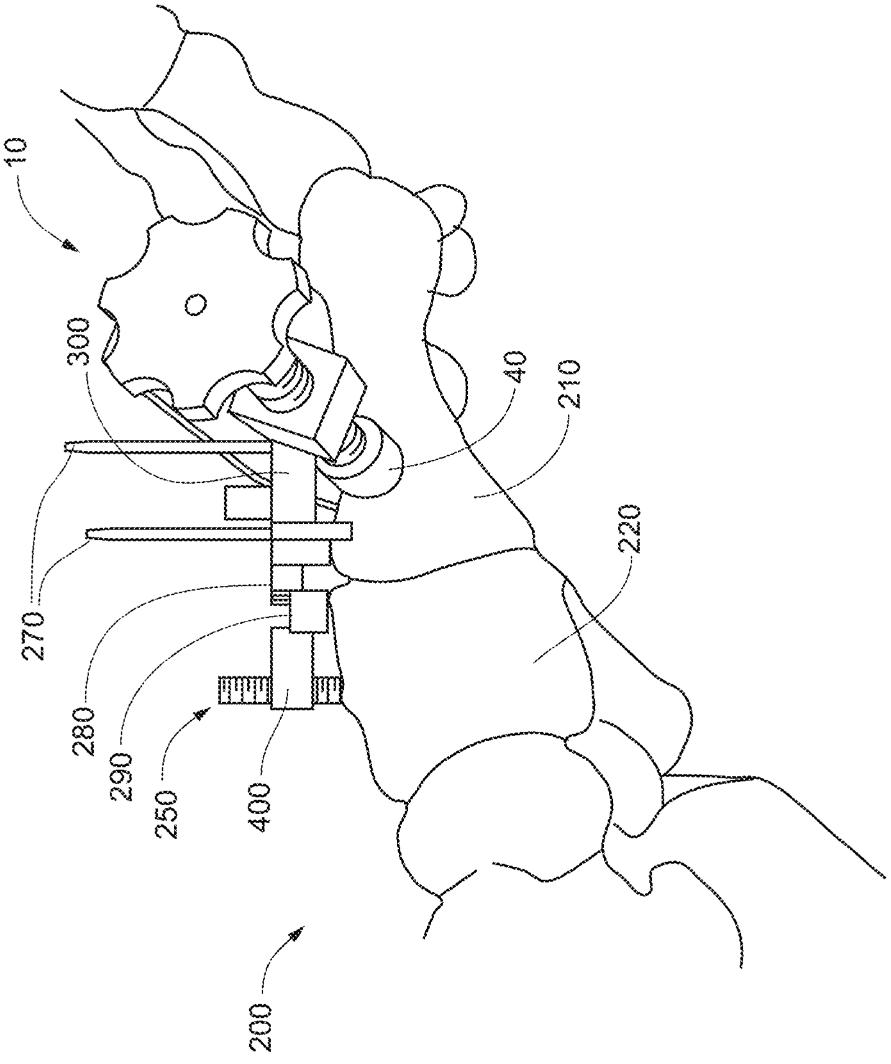
FIG. 10 is a perspective view of a bone cutting guide and a bone positioning guide on a foot positioned for a second bone cut in accordance with an embodiment of the invention.
Figure 11:
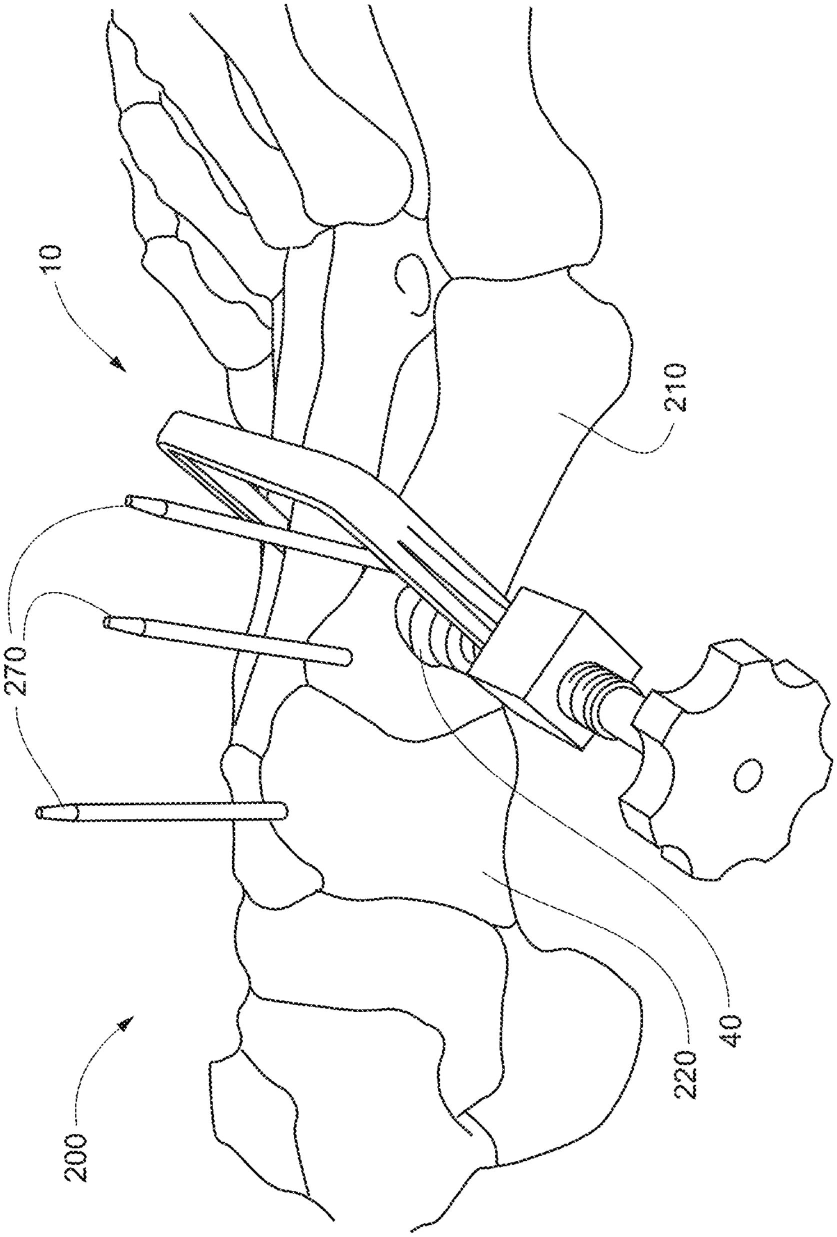
FIG. 11 is a perspective view of a bone positioning guide on a foot in accordance with an embodiment of the invention.
Figure 12:
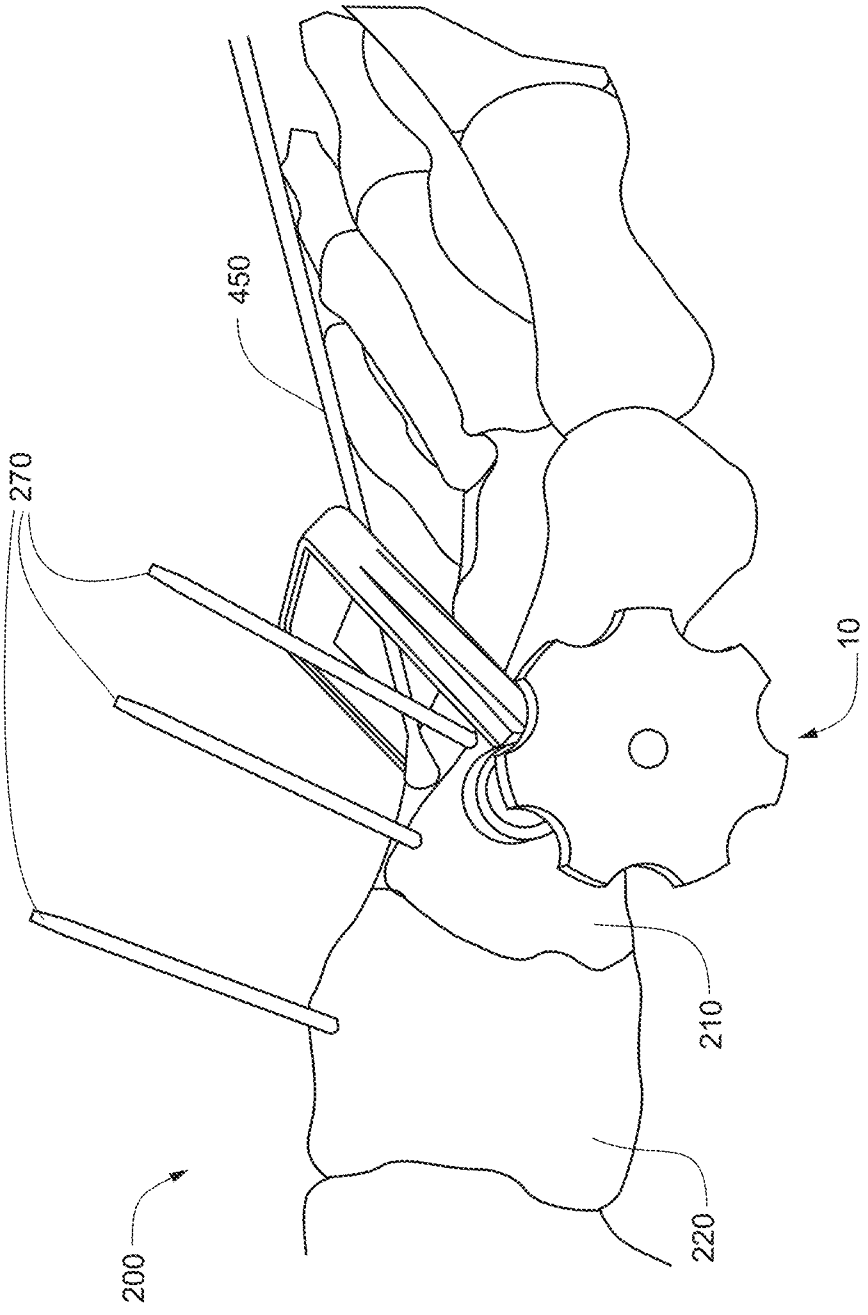
FIG. 12 is a side perspective view of a bone positioning guide on a foot depicting an olive pin providing compression between first and second bones in accordance with an embodiment of the invention.
Figure 13:
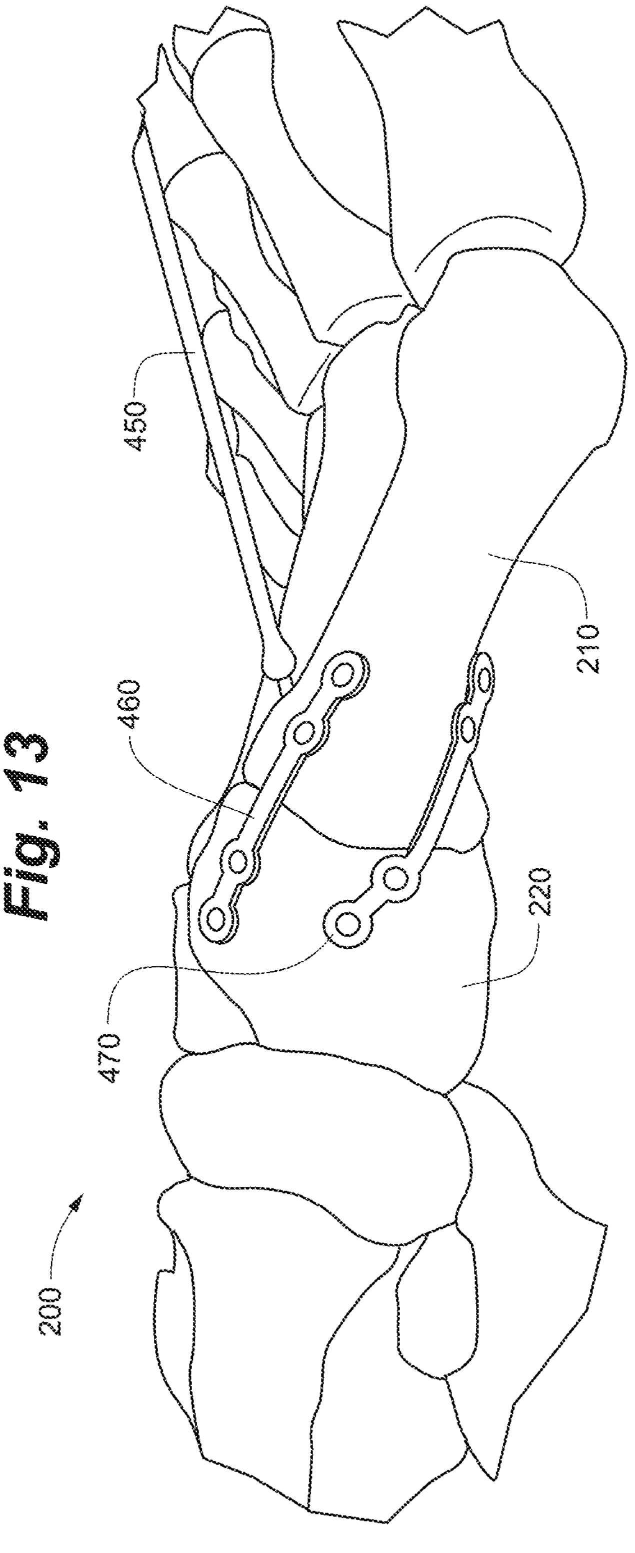
FIG. 13 is a side perspective view of a foot depicting bone plates across a joint between first and second bones in accordance with an embodiment of the invention.

As shown in FIG. 10, the main guide member 280 can be extended from the support 300 to make a parallel cut in the first cuneiform 220. Additional fixation pins 270 can be inserted through apertures in the anchor 400 to fix the cutting guide 250 to the first cuneiform 220. A section of the cuneiform can be cut with a cutting member inserted through the main guide member 280 and removed. In some embodiments the cuneiform cut and the metatarsal cut are parallel, conforming cuts. As shown in FIG. 11, the cutting guide 250 can then be removed with the bone positioning guide 10 in place. FIG. 12 depicts a threaded olive pin 450 inserted through the first metatarsal 210 and into the first cuneiform 220 to provide compression between the first metatarsal and the first cuneiform. The bone positioning guide may then be removed. The position of the bones can then be fixed with a bone screw and/or one or more bone plates of any shape. FIG. 13 shows a first bone plate 460 (e.g., a straight or curved bone plate positioned on a dorsal-medial side) and a second bone plate 470 (e.g., a helical bone plate positioned from a medial side of the cuneiform to a plantar side of the metatarsal (other embodiments, not shown, may include a second straight or curved bone plate)) across the joint space. After the screws are inserted and/or the plates are applied with the insertion of bone screws, the fixation and olive pins may be removed.

Additional details on example surgical technical techniques that can be performed using a bone cutting guide in accordance with the disclosure, as well as details on example features that can be used in conjunction with such bone cutting guide, are described in U.S. patent application Ser. No. 14/981,335, entitled "BONE POSITIONING AND PREPARING GUIDE SYSTEMS AND METHODS" and filed on Dec. 28, 2015, and U.S. patent application Ser. No. 14/990,368, entitled "BONE PLATING SYSTEM AND METHOD" and filed on Jan. 7, 2016, the entire contents of both of which are incorporated herein by reference.

Thus, embodiments of the invention are disclosed. Although the present invention has been described with reference to certain disclosed embodiments, the disclosed embodiments are presented for purposes of illustration, and not limitation, and other embodiments of the invention are possible. One skilled in the art will appreciate that various changes, adaptations, and modifications may be made without departing from the spirit of the invention.

The invention claimed is:

1. A method of correcting a bunion comprising:
- fixating a main body of a guide to a medial cuneiform and/or a first metatarsal;
- positioning a slot of the guide relative to a joint between the first metatarsal and the medial cuneiform;
- locking a location of the slot relative to the main body;
- inserting a cutting member through the slot to prepare an end of the medial cuneiform;
- moving a bone positioning member of a bone positioning guide located on a medial side of the first metatarsal laterally to move the first metatarsal to correct a transverse plane deformity caused by a bunion;
- applying a rotational force to a pin inserted into the first metatarsal to move the first metatarsal to correct a frontal plane deformity caused by the bunion; and
- fixating a moved position of the first metatarsal relative to the medial cuneiform.

2. The method of claim 1, wherein fixating the moved position of the first metatarsal relative to the medial cuneiform comprises applying a bone screw.

3. The method of claim 1, further comprising, prior to fixating the moved position of the first metatarsal relative to the medial cuneiform, compressing the first metatarsal and the medial cuneiform together.

4. The method of claim 1, where fixating the main body of the guide to the medial cuneiform and/or the first metatarsal comprises inserting a fixation pin through an aperture of the main body into the medial cuneiform.

5. The method of claim 1, where fixating the main body of the guide to the medial cuneiform and/or the first metatarsal comprises inserting a fixation pin through an aperture of the main body into the first metatarsal.

6. The method of claim 1, wherein locking the location of the slot relative to the main body comprises rotating a shaft.

7. The method of claim 1, further comprising inserting the cutting member through the slot to prepare an end of the first metatarsal.

8. The method of claim 1, wherein the cutting member comprises a saw.

9. The method of claim 1, further comprising, prior to moving the bone positioning member of the bone positioning guide laterally, attaching the bone positioning member to the first metatarsal.

10. The method of claim 1, where positioning the slot of the guide relative to the joint comprises inserting a spacer into the joint and positioning the slot of the guide relative to the joint using the spacer.

11. A method of correcting a bunion comprising:

inserting a spacer into a joint between a first metatarsal and a medial cuneiform;

positioning a slot of a guide relative to the joint using the spacer;

fixating a main body of the guide to the medial cuneiform and/or the first metatarsal using a fixation pin;

locking a location of the slot relative to the main body;

inserting a cutting member through the slot to prepare an end of the medial cuneiform;

moving a bone positioning member of a bone positioning guide located on a medial side of the first metatarsal laterally to move the first metatarsal to correct a transverse plane deformity caused by a bunion;

applying a rotational force to a pin inserted into the first metatarsal to move the first metatarsal to correct a frontal plane deformity caused by the bunion; and fixating a moved position of the first metatarsal relative to the medial cuneiform.

12. The method of claim 11, further comprising, prior to inserting a cutting member through the slot to prepare the end of the medial cuneiform, removing the spacer from the joint.

13. The method of claim 11, wherein fixating the moved position of the first metatarsal relative to the medial cuneiform comprises applying a bone screw.

14. The method of claim 11, further comprising, prior to fixating the moved position of the first metatarsal relative to the medial cuneiform, compressing the first metatarsal and the medial cuneiform together.

15. The method of claim 11, where fixating the main body of the guide to the medial cuneiform and/or the first metatarsal comprises inserting a fixation pin through an aperture of the main body into the medial cuneiform.

16. The method of claim 11, where fixating the main body of the guide to the medial cuneiform and/or the first metatarsal comprises inserting a fixation pin through an aperture of the main body into the first metatarsal.

17. The method of claim 11, wherein locking the location of the slot relative to the main body comprises rotating a shaft.

18. The method of claim 11, further comprising inserting the cutting member through the slot to prepare an end of the first metatarsal.

19. The method of claim 11, wherein the cutting member comprises a saw.

20. The method of claim 11, further comprising, prior to moving the bone positioning member of the bone positioning guide laterally, attaching the bone positioning member to the first metatarsal.

* * * * *